United States Patent
Asaoka et al.

(10) Patent No.: US 8,410,076 B2
(45) Date of Patent: Apr. 2, 2013

(54) CATIONIZED HYALURONIC ACID AND/OR SALT THEREOF, METHOD OF PRODUCING THE SAME, HAIR MODIFYING AGENT, CUTICLE REPAIRING AGENT, SKIN MODIFYING AGENT, AND COSMETIC PREPARATION EACH USING THE SAME

(75) Inventors: Kazunori Asaoka, Hachioji (JP); Shunichi Fujikawa, Fuchu (JP); Tomoyuki Kanemitsu, Hachioji (JP); Wakako Sakamoto, Tokyo (JP)

(73) Assignee: Q.P. Corporation (JP)

( * ) Notice: Subject to any disclaimer, the term of this patent is extended or adjusted under 35 U.S.C. 154(b) by 263 days.

(21) Appl. No.: 12/597,315

(22) PCT Filed: Apr. 23, 2008

(86) PCT No.: PCT/JP2008/057832
§ 371 (c)(1),
(2), (4) Date: Apr. 2, 2010

(87) PCT Pub. No.: WO2008/133267
PCT Pub. Date: Nov. 6, 2008

(65) Prior Publication Data
US 2010/0197904 A1    Aug. 5, 2010

(30) Foreign Application Priority Data
Apr. 24, 2007   (JP) ................................ 2007-113921

(51) Int. Cl.
*A61K 31/728* (2006.01)
*A61K 31/715* (2006.01)
*C07H 5/06* (2006.01)
*C08B 37/08* (2006.01)

(52) U.S. Cl. .......... 514/54; 536/53; 536/18.7; 536/55.1; 536/55.3

(58) Field of Classification Search .................. 514/54; 536/53, 18.7, 55.1, 55.3
See application file for complete search history.

(56) References Cited

U.S. PATENT DOCUMENTS
4,851,521 A * 7/1989 della Valle et al. .......... 536/55.1
2009/0281056 A1   11/2009 Mori et al.

FOREIGN PATENT DOCUMENTS

| JP | 55-36412 A | 3/1980 |
|---|---|---|
| JP | 55-45602 A | 3/1980 |
| JP | 06-48918 A | 2/1994 |
| JP | 06-087726 A | 3/1994 |
| JP | 10-36403 A | 2/1998 |
| JP | 2003-064102 A | 3/2003 |
| JP | 2003-238385 A | 8/2003 |
| JP | 2006-248932 | 9/2006 |
| JP | 2006-312725 | 11/2006 |
| WO | 2006-018322 | 2/2006 |
| WO | WO 2007/063725 A1 | 6/2007 |

OTHER PUBLICATIONS

Mori et al.; JP 2007-153944; Jun. 21, 2007 (Machine English Translation).*
Carbohydrate Polymers 62 (2005) 321-326.*
Yasuhiro et al.; JP 06087726 A; Mar. 29, 1994 (Machine English Translation).*
Mitsuo et al. (JP 06048918 A; Feb. 22, 1994 (Machine English Translation).*
International Search Report from PCT/JP2008/057832, mailed Jun. 10, 2008.
BASF Japan, Kation-sei Shoho ni Taio sum Hyaluronic Acid 'HA-Quat™ (Quat)', Fragrance Journal, Jun. 15, 2007, vol. 35, No. 6, pp. 127-128.
English Translation of International Preliminary Report on Patentability for PCT/JP2008/057832 (Nov. 10, 2009).
English Translation of Chinese Office Action for Application No. 2008-80013002.7 (Sep. 1, 2011).
English Translation of Chinese Office Action for Application No. 2008-80013002.7 (Mar. 22, 2012).
Japanese Office Action for Application No. 2009-511882 mailed Nov. 6, 2012 (4 pages).
Renae Canterbery Pepe et al., "International Cosmetic Ingredient Dictionary and Handbook", Ninth Edition, vol. 1, Published by The Cosmetic, Toiletry, and Fragrance Association, Washington, D.C., 2002, p. 788.
Fujikawa, Shun-ichi, "Experimental Report 1", Kewpie Corporation, R&D Division, Experiment Date: Feb. 9, 2007 and Feb. 10, 2007, Submitted to Japanese Patent Office on Jan. 7, 2013 (6 pages) with English translation.
Fujikawa, Shun-ichi, "Experimental Report 2", Kewpie Corporation, R&D Division, Experiment Date: Dec. 1, 2007, submitted to Japanese Patent Office on Jan. 7, 2013 (5 pages) with English Translation.

* cited by examiner

*Primary Examiner* — Shaojia Anna Jiang
*Assistant Examiner* — Michael C Henry
(74) *Attorney, Agent, or Firm* — Harness, Dickey & Pierce, P.L.C.

(57) ABSTRACT

A cationized hyaluronic acid and/or a salt thereof includes a quaternary ammonium group-containing group, and has a degree of cationization of 0.15 to 0.6.

22 Claims, 8 Drawing Sheets

CATIONIZED HYALURONIC ACID AND/OR SALT THEREOF, METHOD OF PRODUCING THE SAME, HAIR MODIFYING AGENT, CUTICLE REPAIRING AGENT, SKIN MODIFYING AGENT, AND COSMETIC PREPARATION EACH USING THE SAME

TECHNICAL FIELD

The present invention relates to a cationized hyaluronic acid and/or a salt thereof, a method of producing the same, a hair modifying agent, a cuticle repairing agent, a skin modifying agent, and a cosmetic preparation using the cationized hyaluronic acid and/or a salt thereof.

BACKGROUND ART

Hyaluronic acid is a mucopolysaccharide that is abundantly present in various tissues (e.g., subcutaneous tissues, eyeballs, and joints) of a living body. Hyaluronic acid has been widely used as a cosmetic component due to a high moisturizing effect. For example, Japanese Patent No. 3221533 discloses a hair treatment agent that contains hyaluronic acid.

The surface of hair or skin is normally negatively charged. Hyaluronic acid is also normally negatively charged due to the presence of an anionic functional group (e.g., carboxyl group). Therefore, when treating hair using hyaluronic acid, hyaluronic acid and the hair repel each other since the surface of the hair and hyaluronic acid are negatively charged. Therefore, hyaluronic acid normally adheres to the surface of hair or skin to only a small extent. Accordingly, hyaluronic acid and a salt thereof that exhibit excellent adhesion to a living tissue (e.g., hair or skin) and exhibit a high moisturizing effect have been desired.

DISCLOSURE OF THE INVENTION

An object of the invention is to provide a cationized hyaluronic acid and/or a salt thereof that exhibits excellent adhesion to a living tissue, a method of producing the same, a hair modifying agent, a cuticle repairing agent, a skin modifying agent, and a cosmetic preparation using the cationized hyaluronic acid and/or a salt thereof.

According to one aspect of the invention, there is provided a cationized hyaluronic acid and/or a salt thereof comprising a quaternary ammonium group-containing group and having a degree of cationization of 0.15 to 0.6.

In the above cationized hyaluronic acid and/or salt thereof, the quaternary ammonium group-containing group may be shown by the following general formula (1),

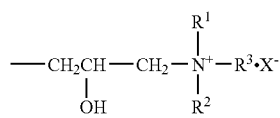

(1)

wherein $R^1$ to $R^3$ individually represent hydrocarbon groups, and $X^-$ represents a monovalent anion.

In the above cationized hyaluronic acid and/or salt thereof, the quaternary ammonium group-containing group may be bonded to an oxygen atom of a (—C(=O)O—) group.

In this case, the quaternary ammonium group-containing group may be obtained by reacting a carboxyl group included in hyaluronic acid and/or a salt thereof with a cationizing agent that contains a quaternary ammonium group.

In this case, the cationizing agent may be at least one of a 2,3-epoxypropyltrialkylammonium halide and a 3-halogeno-2-hydroxypropyltrialkylammonium halide.

According to a second aspect of the invention, there is provided a hair modifying agent comprising the above cationized hyaluronic acid and/or salt thereof.

In the above hair modifying agent, the cationized hyaluronic acid and/or a salt thereof may have a degree of cationization of 0.15 to 0.4.

The above hair modifying agent may be used for a leave-in hair cosmetic preparation, and the cationized hyaluronic acid and/or a salt thereof may have a degree of cationization of 0.15 to 0.4 and a kinematic viscosity (0.2% aqueous solution) of 5 to 50 $mm^2/s$.

The above hair modifying agent may be used for a rinse-out hair cosmetic preparation, and the cationized hyaluronic acid and/or a salt thereof may have a degree of cationization of 0.4 to 0.6 and a kinematic viscosity (0.2% aqueous solution) of 1 to 20 $mm^2/s$.

The above hair modifying agent may be used as a cuticle repairing agent.

According to a third aspect of the invention, there is provided a skin modifying agent comprising the above cationized hyaluronic acid and/or salt thereof.

According to a fourth aspect of the invention, there is provided a skin modifying agent comprising the above cationized hyaluronic acid and/or salt thereof.

According to a fifth aspect of the invention, there is provided a cosmetic preparation comprising the above cationized hyaluronic acid and/or salt thereof.

According to a sixth aspect of the invention, there is provided a method of producing a cationized hyaluronic acid and/or a salt thereof comprising reacting hyaluronic acid and/or a salt thereof with a cationizing agent in a basic water-containing medium.

The above method of producing a cationized hyaluronic acid and/or a salt thereof may further comprise adding at least one of a sodium salt and a potassium salt to the reaction solution and dissolving a solid produced in the reaction solution after reacting the hyaluronic acid and/or a salt thereof with the cationizing agent, and adding an alcohol to the reaction solution in which the solid is dissolved to obtain a precipitate.

In the above method of producing a cationized hyaluronic acid and/or a salt thereof, the hyaluronic acid and/or a salt thereof may be reacted with the cationizing agent by heating the basic water-containing medium at 30 to 70° C.

According to a seventh aspect of the invention, there is provided a cationized hyaluronic acid and/or a salt thereof shown by the following general formula (2),

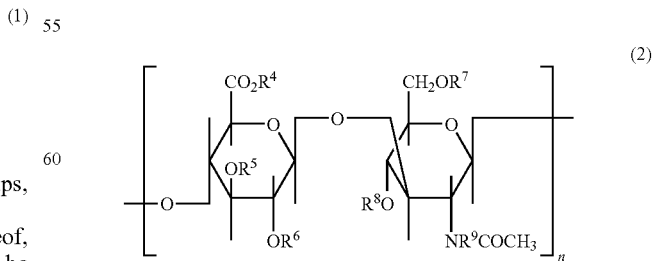

(2)

wherein $R^4$ to $R^9$ individually represent a hydrogen atom or a quaternary ammonium group-containing group (excluding a case where all of $R^4$ to $R^9$ represent hydrogen atoms), and n represents an integer from 2 to 5000.

The above cationized hyaluronic acid and/or a salt thereof may have a degree of cationization of 0.15 to 0.6.

The term "hyaluronic acid" used in the invention refers to a polysaccharide including at least one repeating unit formed of glucuronic acid and N-acetylglucosamine. The term "degree of cationization" of hyaluronic acid and/or a salt thereof used herein refers to the number of quaternary ammonium group-containing groups (number of substitutions) per repeating unit of hyaluronic acid and/or a salt thereof.

The hyaluronic acid salt is not particularly limited. The hyaluronic acid salt is preferably a pharmaceutically acceptable salt. Examples of the hyaluronic acid salt include a sodium salt, a potassium salt, a calcium salt, a zinc salt, a magnesium salt, an ammonium salt, and the like of hyaluronic acid.

Since the above cationized hyaluronic acid and/or a salt thereof includes a quaternary ammonium group-containing group and has a degree of cationization of 0.15 to 0.6, the cationized hyaluronic acid and/or a salt thereof is positively charged while maintaining the characteristics of hyaluronic acid. Therefore, the cationized hyaluronic acid and/or a salt thereof exhibits excellent adhesion to a living tissue (e.g., the surface of hair or skin) and an excellent moisturizing effect, hair, skin, and the like can be smoothed. Accordingly, the above cationized hyaluronic acid and/or a salt thereof is useful as a component of a hair modifying agent, a cuticle repairing agent, a skin modifying agent, or a cosmetic preparation, for example.

BEST MODE FOR CARRYING OUT THE INVENTION

Figure 1:
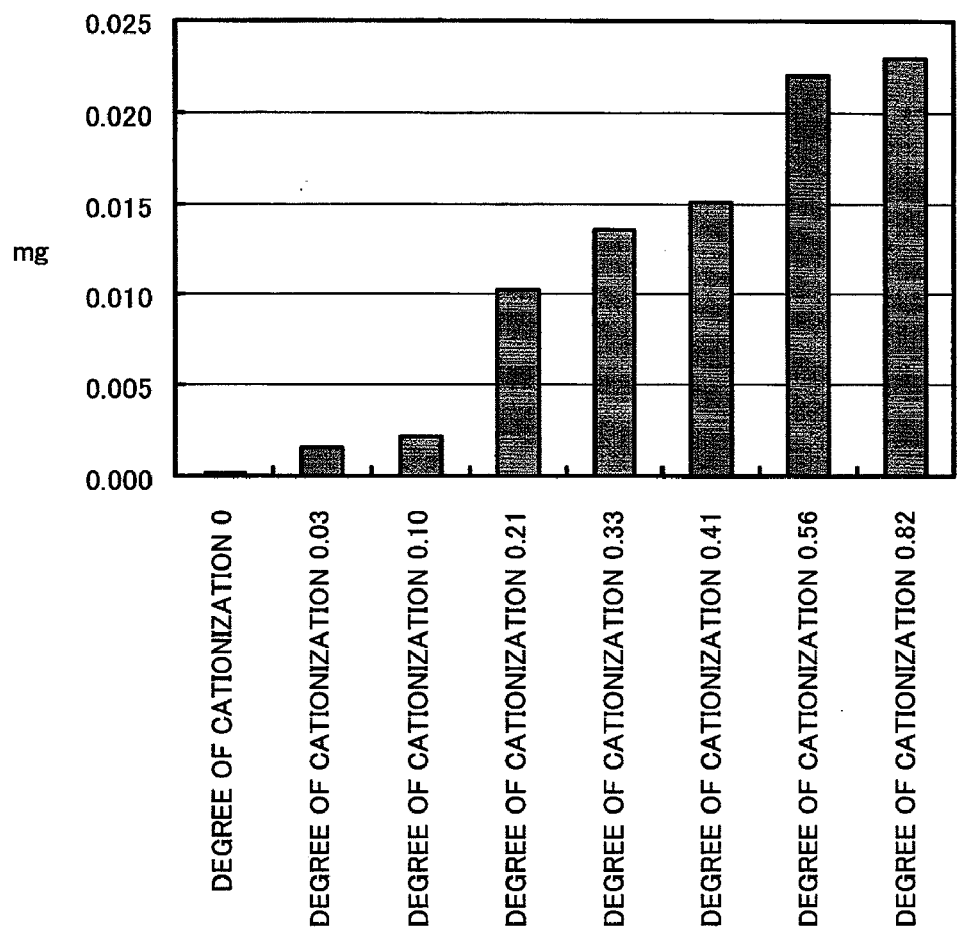
FIG. 1 is a graph showing the amount of each sample adhering to 1 g of hair determined in Test Example 1.

A cationized hyaluronic acid and/or a salt thereof according to one embodiment of the invention, a method of producing the same, a hair modifying agent, a cuticle repairing agent, a skin modifying agent, and a cosmetic preparation using the cationized hyaluronic acid and/or a salt thereof are described in detail below. In the following embodiments and examples, the unit "%" refers to "mass %".

1. Cationized Hyaluronic Acid and/or Salt Thereof

The cationized hyaluronic acid and/or a salt thereof according to this embodiment includes a quaternary ammonium group-containing group, and has a degree of cationization of 0.15 to 0.6. If the cationized hyaluronic acid and/or a salt thereof has a degree of cationization of less than 0.15, adhesion of the cationized hyaluronic acid and/or a salt thereof to a living tissue (e.g., hair or skin) may decrease to a large extent, so that a sufficient moisturizing effect may not be obtained. If the cationized hyaluronic acid and/or a salt thereof has a degree of cationization of more than 0.6, the cationized hyaluronic acid and/or a salt thereof adheres to hair or skin, but may not achieve a sufficient moisturizing effect and smoothness.

In order to achieve more excellent adhesion and a more excellent moisturizing effect to reduce hair dryness/roughness and skin dryness, it is preferable that the cationized hyaluronic acid and/or a salt thereof according to this embodiment have a degree of cationization of 0.15 to 0.4.

The term "hair dryness" used herein refers to the state of the hair when the hair is harsh to the touch due to a low water content, the term "hair roughness" used herein refers to the state of the hair when the hair is rough to the touch, and the term "skin dryness" used herein refers to the state of the skin when the skin is harsh to the touch due to a low water content.

1.1. Quaternary Ammonium Group-Containing Group

The term "quaternary ammonium group-containing group" refers to a group that at least partially contains a quaternary ammonium group. The quaternary ammonium group-containing group may a group shown by the following general formula (1), for example.

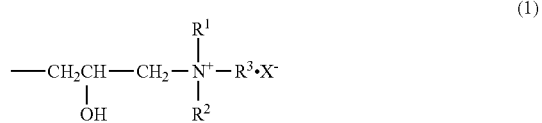

wherein $R^1$ to $R^3$ individually represent hydrocarbon groups, and $X^-$ represents a monovalent anion.

Examples of the hydrocarbon groups represented by $R^1$ to $R^3$ in the general formula (1) include a linear or branched alkyl group, an unsaturated hydrocarbon group, and an aromatic hydrocarbon group. Among these, the alkyl group is preferable. Examples of the alkyl group include alkyl groups having 1 to 30 (preferably 1 to 6) carbon atoms. It is more preferable that the hydrocarbon groups represented by $R^1$ to $R^3$ be alkyl groups having 1 to 3 carbon atoms.

Examples of the monovalent anion represented by $X^-$ in the general formula (1) include a halogen ion such as a fluorine ion, a bromine ion, a chlorine ion, and an iodine ion.

The quaternary ammonium group-containing group may be introduced by replacing the hydrogen atom of the carboxyl group included in hyaluronic acid and/or a salt thereof used as a raw material (hereinafter may be referred to as "raw material hyaluronic acid and/or a salt thereof") with the quaternary ammonium group-containing group. In this case, the quaternary ammonium group-containing group is bonded to the oxygen atom of the group (—C(=O)O—) included in the cationized hyaluronic acid and/or a salt thereof according to this embodiment. The fact that the quaternary ammonium group-containing group is bonded to the oxygen atom of the group (—C(=O)O—) included in the cationized hyaluronic acid and/or a salt thereof according to this embodiment may be confirmed by the presence of a peak attributed to the carbon atom of the —C(=O)O— group to which the quaternary ammonium group-containing group is bonded via the oxygen atom, determined by analyzing the chemical shift of the nuclear magnetic resonance ($^{13}$C NMR) spectrum.

Specifically, the quaternary ammonium group-containing group may be obtained by reacting the carboxyl group (and/or hydroxyl group) of the raw material hyaluronic acid and/or a salt thereof with a cationizing agent that contains a quaternary ammonium group. It is preferable that the cationizing agent is at least one of a 2,3-epoxypropyltrialkylammonium halide shown by the following general formula (3) and a 3-halogeno-2-hydroxypropyltrialkylammonium halide shown by the following general formula (4). The reaction of the raw material hyaluronic acid and/or a salt thereof with the cationizing agent is described in the production method hereinafter.

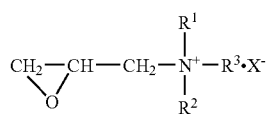

(3)

wherein $R^1$ to $R^3$ are the same as defined for the general formula (1), and X represents a halogen atom.

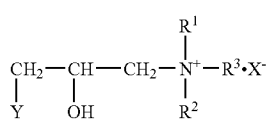

(4)

wherein $R^1$ to $R^3$ are the same as defined for the general formula (1), and X and Y individually represent halogen atoms.

Examples of the halogen atoms represented by X and Y in the general formulas (3) and (4) include a fluorine atom, a bromine atom, a chlorine atom, and an iodine atom.

1.2. Degree of Cationization

The degree of cationization (i.e., the degree of substitution with the quaternary ammonium group-containing group) of the cationized hyaluronic acid and/or a salt thereof according to this embodiment may be determined by calculating the nitrogen content of raw material sodium hyaluronate and the nitrogen content of the cationized hyaluronic acid by the semi-micro Kjeldahl method, and calculating the degree of cationization by the following expression based on the increase in the nitrogen content.

When the nitrogen content of the raw material sodium hyaluronate is referred to as $N_N$ (%) and the nitrogen content of the cationized hyaluronic acid having a degree of cationization of (x) is referred to as $N_S$ (%), the relationship between the increase in the nitrogen content ($N_S-N_N$) and the degree of cationization (x) is shown by the following expression.

$N_S-N_N$(%)

=[14x/(molecular weight of disaccharide unit of cationized hyaluronic acid)]×100

=[14x/(molecular weight of disaccharide unit of raw material sodium hyaluronate)+129.5x]×100

=[14x/(401.3+129.5x)]×100

Therefore, the degree of cationization (i.e., the degree of substitution with the quaternary ammonium group-containing group) can be calculated by the following expression.

Degree of cationization(x)=[($N_S-N_N$)×401.3]/[1400−129.5×($N_S-N_N$)]

The degree of cationization of a cationized hyaluronic acid when a raw material hyaluronic acid is unknown may be calculated by the above expression on the assumption that the raw material sodium hyaluronate is sodium hyaluronate having a purity of 99% or more.

1.3. Characteristics

The cationized hyaluronic acid and/or a salt thereof according to this embodiment exhibits excellent adhesion to a living tissue (e.g., hair, eyelashes, eyebrows, nail, and skin). The cationized hyaluronic acid and/or a salt thereof according to this embodiment may be applied to or caused to come in contact with the surface of a living tissue. Since the cationized hyaluronic acid and/or a salt thereof according to this embodiment exhibits excellent adhesion to hair, eyelashes, eyebrows or skin (e.g., face, arm, finger, foot, or joint), the cationized hyaluronic acid and/or a salt thereof is preferably applied to or caused to come in contact with hair or skin.

The average molecular weight of the cationized hyaluronic acid and/or a salt thereof according to this embodiment is preferably 800 to 2,500,000, and more preferably 50,000 to 1,500,000, from the viewpoint of a hair/skin modification effect and mixing into a cosmetic preparation.

1.4. Structure of Cationized Hyaluronic Acid and/or Salt Thereof

The cationized hyaluronic acid and/or a salt thereof according to this embodiment may have a structure shown by the following general formula (2).

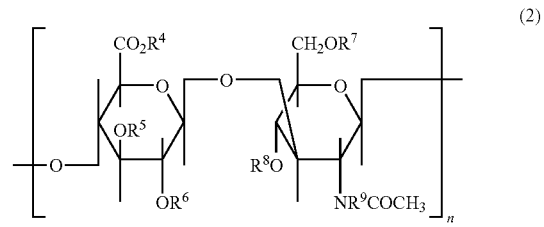

(2)

wherein $R^4$ to $R^9$ individually represent a hydrogen atom or a quaternary ammonium group-containing group (excluding a case where all of $R^4$ to $R^9$ represent hydrogen atoms), and n represents an integer from 2 to 5000.

Examples of the quaternary ammonium group-containing group represented by $R^4$ to $R^9$ in the general formula (2) include groups shown by the following general formula (5).

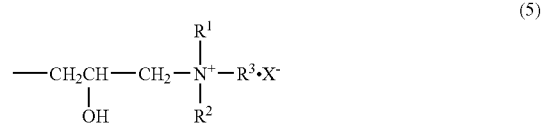

(5)

wherein $R^1$ to $R^3$ are the same as defined for the general formula (1).

Examples of the groups represented by $R^1$ to $R^3$ and $X^-$ include the groups mentioned above as examples of the groups represented by $R^1$ to $R^3$ and $X^-$ in the general formula (1).

2. Hair Modifying Agent

A hair modifying agent according to one embodiment of the invention includes the cationized hyaluronic acid and/or a salt thereof. The degree of cationization of the cationized hyaluronic acid and/or a salt thereof included in the hair modifying agent according to this embodiment is preferably 0.15 to 0.6, and more preferably 0.15 to 0.4. If the cationized hyaluronic acid and/or a salt thereof has a degree of cationization of less than 0.15, the cationized hyaluronic acid and/or a salt thereof may not sufficiently adhere to hair so that a sufficient moisturizing effect and smoothness may not be obtained. If the cationized hyaluronic acid and/or a salt thereof has a degree of cationization of more than 0.6, the cationized hyaluronic acid and/or a salt thereof adheres to hair, but may not achieve a sufficient moisturizing effect and smoothness.

The hair modifying agent according to this embodiment may be used as a cuticle repairing agent, for example.

Examples of the hair modifying agent according to this embodiment include a rinse-out hair cosmetic preparation and a leave-in hair cosmetic preparation. The term "leave-in hair cosmetic preparation" used herein refers to a cosmetic preparation that is applied to hair and is not washed away. Examples of the leave-in hair cosmetic preparation include an undiluted hair conditioner, hair cream, hair styling agent, hair wax, hair gel, hair foam (hair mousse), hair lotion, hair spray, hair oil, hair tonic, baldness remedy, permanent liquid, mascara, eyeliner, eyebrow liner, and the like. The term "rinse-out hair cosmetic preparation" used herein refers to a cosmetic preparation that is applied to hair and then washed away. Examples of the rinse-out hair cosmetic preparation include a shampoo, rinse, rinse-in-shampoo, hair conditioner, hair pack, mascara cleansing agent, hair color pretreatment liquid, coloring liquid, and the like.

When the hair modifying agent according to this embodiment is used as a leave-in hair cosmetic preparation, it is preferable that the cationized hyaluronic acid and/or a salt thereof included in the cosmetic preparation have a degree of cationization of 0.15 to 0.4 and a kinematic viscosity (0.2% aqueous solution) of 5 to 50 mm$^2$/s. A leave-in hair cosmetic preparation that includes the cationized hyaluronic acid and/or a salt thereof having a degree of cationization and a kinematic viscosity within the above ranges has a moderate viscosity and exhibits excellent adhesion to hair. Therefore, hair can be moisturized and provided with an improved feel. Moreover, dryness and roughness of hair can be suppressed in a state in which the hair cosmetic preparation is not washed away.

When the hair modifying agent according to this embodiment is used as a rinse-out hair cosmetic preparation, it is preferable that the cationized hyaluronic acid and/or a salt thereof included in the cosmetic preparation have a degree of cationization of 0.4 to 0.6 and a kinematic viscosity (0.2% aqueous solution) of 1 to 20 mm$^2$/s. A rinse-out hair cosmetic preparation that includes the cationized hyaluronic acid and/or a salt thereof having a degree of cationization and a kinematic viscosity within the above ranges exhibits excellent adhesion to hair. Therefore, hair can be moisturized and provided with an improved feel. Moreover, dryness and roughness of hair can be suppressed after the hair cosmetic preparation has been washed away.

The kinematic viscosity of the cationized hyaluronic acid and/or a salt thereof may be measured using an Ubbelohde viscometer (manufactured by Sibata Scientific Technology Ltd.). In this case, an Ubbelohde viscometer having such a coefficient that the falling time is 200 to 1000 seconds is selected. The kinematic viscosity is measured in a incubator at 30° C. while maintaining a constant temperature.

The kinematic viscosity (mm$^2$/s) can be calculated by multiplying the falling time (sec) of the aqueous solution measured using the Ubbelohde viscometer by the coefficient of the Ubbelohde viscometer.

3. Skin Modifying Agent

A skin modifying agent according to one embodiment of the invention includes the cationized hyaluronic acid and/or a salt thereof. The degree of cationization of the cationized hyaluronic acid and/or a salt thereof included in the skin modifying agent according to this embodiment is preferably 0.15 to 0.6, and more preferably 0.3 to 0.6. If the cationized hyaluronic acid and/or a salt thereof has a degree of cationization of less than 0.15, the cationized hyaluronic acid and/or a salt thereof may not sufficiently adhere to skin so that a sufficient moisturizing effect and smoothness may not be obtained. If the cationized hyaluronic acid and/or a salt thereof has a degree of cationization of more than 0.6, the cationized hyaluronic acid and/or a salt thereof adheres to skin, but may not achieve a sufficient moisturizing effect and smoothness. Examples of the skin modifying agent according to this embodiment include a skin cosmetic preparation. A skin cosmetic preparation that includes the cationized hyaluronic acid and/or a salt thereof having a degree of cationization and a kinematic viscosity within the above ranges has a moderate viscosity and exhibits excellent adhesion to skin. Therefore, skin can be moisturized and provided with an improved feel. Moreover, dryness of skin can be suppressed. Examples of the skin cosmetic preparation according to this embodiment include a facial wash, a skin cleansing preparation, toilet lotion (e.g., whitening lotion), cream (e.g., vanishing cream and cold cream), milky lotion, essence, pack (e.g., jellied pack, paste pack, and powdery pack), a cleansing product, foundation, rouge, lip balm, lip gloss, lip liner, cheek rouge, after-shave lotion, after-sun lotion, deodorant lotion, body lotion (including hand care lotion and foot care lotion), body oil, soap, body soap, bath additive, and the like.

4. Cosmetic Preparation

A cosmetic preparation according to one embodiment of the invention includes the hair modifying agent or the skin modifying agent. The cosmetic preparation according to this embodiment may include the cationized hyaluronic acid and/or a salt thereof as a moisturizer. The cosmetic preparation according to this embodiment normally includes the cationized hyaluronic acid and/or a salt thereof in an amount of 0.001 to 5%. If the amount of the cationized hyaluronic acid and/or a salt thereof is less than 0.001%, a sufficient moisturizing effect and smoothness may not be obtained so that dryness/roughness of hair or dryness of skin may not be suppressed. If the amount of the cationized hyaluronic acid and/or a salt thereof is more than 5%, it may be difficult to spread the cosmetic preparation over the entire hair or skin due to an increase in viscosity.

Examples of the cosmetic preparation according to this embodiment include a hair cosmetic preparation, a skin cosmetic preparation, and a nail cosmetic preparation. Examples of the hair cosmetic preparation include the rinse-out hair cosmetic preparation and the leave-in hair cosmetic preparation mentioned above.

Examples of the skin cosmetic preparation include the above-mentioned skin cosmetic preparations and the like.

Examples of the nail cosmetic preparation include a nail conditioner and a nail paint remover.

Since the cosmetic preparation according to this embodiment includes the cationized hyaluronic acid and/or a salt thereof, the cosmetic preparation exhibits excellent adhesion to a living tissue and therefore exhibits an excellent moisturizing effect. In particular, the cosmetic preparation according to this embodiment exhibits excellent adhesion to a living tissue (e.g., hair or skin) having a negatively charged surface due to the cationized hyaluronic acid and/or salt thereof. Therefore, the cosmetic preparation according to this embodiment exhibits excellent affinity to a damaged area of hair.

Since the cosmetic preparation according to this embodiment includes the cationized hyaluronic acid and/or a salt thereof, the cosmetic preparation has a moderate viscosity. Therefore, dryness/roughness of hair or dryness of skin can be suppressed.

Therefore, the cosmetic preparation according to this embodiment can moisturize hair or skin and suppress dryness/roughness of hair or dryness of skin due to the cationized hyaluronic acid and/or a salt thereof.

The cosmetic preparation according to this embodiment may further include a cationized polysaccharide (e.g., cationized hydroxyethyl cellulose, cationized guar gum, cationized starch, cationized locust bean gum, cationized dextran, cationized chitosan, and cationized honey), an anionic surfactant (e.g., alkylbenzenesulfonate, polyoxyalkylenealkyl sulfate salt, alkyl sulfate salt, olefin sulfonate, fatty acid salt, and dialkylsulfosuccinate), a nonionic surfactant (e.g., polyoxyethylene fatty acid ester and polyoxyethylene hydrogenated castor oil derivative), a cationic surfactant (e.g., alkyltrimethylammonium salt, dialkyldimethylammonium salt, alkylpyridinium salt, and stearyltrimethylammonium chloride), an amphoteric surfactant (e.g., alkyl betaine, alkylamide propyl betaine, imidazolinium betaine, egg-yolk lecithin, and soybean lecithin), oils (e.g., silicone, silicone derivative, liquid paraffin, squalane, yellow bees wax, carnauba wax, olive oil, avocado oil, camellia oil, jojoba oil, and horse oil), a moisturizer (e.g., sodium hyaluronate, hydrolyzed hyaluronic acid, acetylated hyaluronic acid, dimethylsilanol hyaluronate, ceramide, phytoglycogen, hydrolyzed eggshell membrane, trehalose, glycerol, atelocollagen, sorbitol, maltitol, and 1,3-butylene glycol), a higher fatty acid (e.g., lauric acid, behenic acid, palmitic acid, stearic acid, isostearic acid, and oleic acid), a higher alcohol (e.g., cetyl alcohol, stearyl alcohol, behenyl alcohol, isostearyl alcohol, and batyl alcohol), a polyhydric alcohol (e.g., glycerol, diglycerol, propylene glycol, polyethylene glycol, and pentylene glycol), a thickener (e.g., cellulose ether, carboxyvinyl polymer, xanthan gum, and dextrin palmitate), an amphoteric polymer resin compound (e.g., betaine dialkylaminoalkyl acrylate copolymer), a cationic polymer resin compound (e.g., cationized vinylpyrrolidone/dimethylaminoethyl methacrylate copolymer and polydimethyldiallylammonium halide cationic polymer), a preservative (e.g., methylparaben, ethylparaben, butylparaben, propylparaben, and phenoxyethanol), an antioxidant (e.g., tocopherol and BHT), a sequestering agent (e.g., edetate and etidronic acid salt), a UV absorber (e.g., benzophenone derivative, p-aminobenzoic acid derivative, and methoxycinnamic acid derivative), a UV reflection agent (e.g., titanium oxide and zinc oxide), a protein hydrolyzate (e.g., keratin peptide, collagen peptide, soybean peptide, wheat peptide, milk peptide, silk peptide, and egg white peptide), an amino acid (e.g., arginine, glutamic acid, glycine, alanine, hydroxyproline, cysteine, serine, and L-theanine), a natural extract (Sophorae radix extract, chamomile extract, seaweed extract, eucalyptus extract, royal jelly extract, *Rosmarinus officinalis* L. extract, and beech extract), other functional components (coenzyme Q10, arbutin, polyquaternium-51, elastin, platinum nanocolloid, retinol palmitate, panthenol, allantoin, and sodium lysine dilauroyl glutamate), a phospholipid polymer, essence, and a dye.

5. Method of Producing Cationized Hyaluronic Acid and/or Salt Thereof

A method of producing a cationized hyaluronic acid and/or a salt thereof according to one embodiment of the invention includes reacting a raw material hyaluronic acid and/or a salt thereof with a cationizing agent in a basic water-containing medium. A cationized hyaluronic acid and/or a salt thereof having a degree of cationization of 0.15 to 0.6 can be obtained by this method.

The method of producing a cationized hyaluronic acid and/or a salt thereof according to this embodiment can increase production efficiency as compared with the case of dissolving the raw material hyaluronic acid and/or a salt thereof in water and reacting the raw material hyaluronic acid and/or a salt thereof with the cationizing agent.

5.1. Reaction with Cationizing Agent

In the method of producing a cationized hyaluronic acid and/or a salt thereof according to this embodiment, it is preferable to react the raw material hyaluronic acid and/or a salt thereof with the cationizing agent in a state in which the raw material hyaluronic acid and/or a salt thereof is dispersed in the basic water-containing medium. Specifically, the raw material hyaluronic acid and/or a salt thereof is reacted with the cationizing agent in a state in which most of the raw material hyaluronic acid and/or a salt thereof is not dissolved in the basic water-containing medium. The production efficiency can be increased while improving the progress of hydrolysis of the cationizing agent by reacting the raw material hyaluronic acid and/or a salt thereof with the cationizing agent in a state in which the raw material hyaluronic acid and/or a salt thereof is dispersed in the basic water-containing medium.

The raw material hyaluronic acid and/or a salt thereof may be dispersed in the basic water-containing medium by adding a powdery raw material hyaluronic acid and/or a salt thereof to the basic water-containing medium and stirring the mixture, for example. The powdery hyaluronic acid and/or a salt thereof is dispersed in the basic water-containing medium while being dissolved in the basic water-containing medium to only a small extent.

The degree of cationization may be adjusted by adjusting the reaction conditions (e.g., temperature and time).

The reaction time is normally 0.1 to 6 hours. If the reaction time is less than 0.1 hours, cationization may not sufficiently proceed. If the reaction time is more than 6 hours, the resulting hyaluronic acid and/or a salt thereof may bind depending on the reaction temperature.

5.1.1. Raw Material Hyaluronic Acid and/or Salt Thereof

Hyaluronic acid and/or a salt thereof are generally extracted (and purified, if necessary) from a biological tissue (e.g., cockscomb, umbilical cord, eyeball, skin, or cartilage), or a culture obtained by culturing a hyaluronic acid-producing microorganism (e.g., *Streptococcus* microorganism).

The average molecular weight of the raw material hyaluronic acid and/or a salt thereof is normally 800 to 3,000,000, and preferably 1,000,000 to 2,000,000. A cationized hyaluronic acid that preferably has an average molecular weight of 800 to 2,500,000, and more preferably 50,000 to 1,500,000, can be obtained using the raw material hyaluronic acid having an average molecular weight within the above range.

As the raw material hyaluronic acid and/or a salt thereof, the above-mentioned unpurified extract or a purified product thereof may be used. It is preferable to use a purified product with a purity of hyaluronic acid and/or a salt thereof of 90% (mass %) or more. When using a raw material hyaluronic acid and/or a salt thereof with a purity of 90% or more, the raw material hyaluronic acid and/or a salt thereof rarely cause a change in color tone or flavor during storage. As a result, a stable cosmetic preparation can be obtained.

5.1.2. Heating Temperature

The raw material hyaluronic acid and/or a salt thereof may be reacted with the cationizing agent with heating. Specifically, a dispersion medium obtained by adding the powdery raw material hyaluronic acid and/or a salt thereof to the basic water-containing medium with stirring may be heated. Alternatively, the raw material hyaluronic acid and/or a salt thereof may be added to the basic water-containing medium heated in advance, and the temperature of the mixture may be maintained.

The heating temperature of the basic water-containing medium is preferably 70° C. or less. If the basic water-containing medium is heated to 70° C. or less, a cationized hyaluronic acid and/or a salt thereof having the desired degree of cationization can be obtained by heating the basic water-containing medium for one hour or less. If the heating temperature is higher than 70° C., the resulting cationized hyaluronic acid and/or a salt thereof may bind or brown. The heating temperature of the basic water-containing medium is more preferably 30 to 70° C.

If the heating temperature of the basic water-containing medium is 30 to 60° C., a cationized hyaluronic acid and/or a salt thereof having a degree of cationization of 0.15 to 0.4 can be obtained by heating the basic water-containing medium for one hour or less. If the heating temperature of the basic water-containing medium is 60 to 70° C., a cationized hyaluronic acid and/or a salt thereof having a degree of cationization of 0.4 to 0.6 can be obtained by heating the basic water-containing medium for one hour or less.

5.1.3. Cationizing Agent

Examples of the cationizing agent include a cationizing agent that contains a quaternary ammonium group such as a 2,3-epoxypropyltrialkylammonium halide (glycidyl trialkylammonium salt) shown by the general formula (3) and a 3-halogeno-2-hydroxypropyltrialkylammonium halide shown by the general formula (4). These cationizing agents may be used either individually or in combination.

Specific examples of the cationizing agent (2,3-epoxypropyltrialkylammonium halide) include glycidyltrimethylammonium chloride, glycidyltriethylammonium chloride, glycidyltripropylammonium chloride, glycidyldimethyloctyl ammonium chloride, glycidyldimethyldecylammonium chloride, glycidyldimethyllaurylammonium chloride, glycidyldimethylstearylammonium chloride, and the like.

Examples of the cationizing agent (3-halogeno-2-hydroxypropyltrialkylammonium halide) include 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropyldimethyloctylammonium chloride, 3-chloro-2-hydroxypropyldimethyldecylammonium chloride, 3-chloro-2-hydroxypropyldimethyllaurylammonium chloride, 3-chloro-2-hydroxypropyldimethylstearylammonium chloride, and the like.

The cationizing agent is preferably at least one of 3-chloro-2-hydroxypropyltrimethylammonium chloride and glycidyltrimethylammonium chloride.

The amount of the cationizing agent may be arbitrarily selected depending on the desired degree of cationization. It is preferable to use the cationizing agent in an amount of 0.5 to 4 parts by mass, and more preferably 1 to 3 parts by mass, based on 1 part by mass of hyaluronic acid. If the amount of the cationizing agent is less than 0.5 parts by mass, cationization may not sufficiently proceed. If the amount of the cationizing agent is more than 4 parts by mass, hyaluronic acid may be dissolved in the reaction solution so that the handling capability during purification may deteriorate.

Since the method of producing a cationized hyaluronic acid and/or a salt thereof according to this embodiment includes reacting the raw material hyaluronic acid and/or a salt thereof with the cationizing agent that includes the quaternary ammonium group-containing group in the basic water-containing medium, the hydrogen atom of the carboxyl group included in the hyaluronic acid and/or a salt thereof can be preferentially replaced by the quaternary ammonium group-containing group so that the quaternary ammonium group can be preferentially bonded to the carbonyl group.

5.1.4. Basic Water-Containing Medium

In the present invention, the term "water-containing medium" refers to a water-containing dispersion medium of hyaluronic acid and/or a salt thereof. A medium that dissolves hyaluronic acid and/or a salt thereof to very little or only a small extent may be used as the water-containing medium. A medium that may be used for the water-containing medium is not particularly limited. For example, it is preferable to use a liquid that is dissolved in water and can be used in the production of a cosmetic preparation. Examples of the medium that may be used for the water-containing medium include alcohol media (e.g., methanol, ethanol, n-propanol, and 2-propanol), ketone media (e.g., acetone and methyl ethyl ketone), tetrahydrofuran, acetonitrile, and the like. These media may be used either individually or in combination. The medium is preferably the alcohol medium, more preferably a lower alcohol having 1 to 3 carbon atoms, and still more preferably ethanol, from the viewpoint of a low boiling point and low cost.

The water content of the water-containing medium is preferably 10 to 40 vol %. If the water content of the water-containing medium is more than 40 vol %, since hyaluronic acid and/or a salt thereof may not maintain a dispersion state and may be dissolved in the water-containing medium, cationization may not sufficiently proceed. Moreover, it may be difficult to stir the mixture due to an increase in viscosity. If the water content of the water-containing medium is less than 10 vol %, cationization may not sufficiently proceed.

The basic water-containing medium may be obtained by adding a base to the water-containing medium. The base is not particularly limited, but is preferably a base that can be used in the production of a cosmetic preparation. Examples of the base include sodium hydroxide and potassium hydroxide. The amount of base added to the water-containing medium is not particularly limited. If the amount of base is too small, cationization of hyaluronic acid and/or a salt thereof may not proceed so that the production efficiency may decrease. If the amount of base is too large, cationization and hydrolysis of hyaluronic acid and/or a salt thereof may be excessively promoted so that it may be difficult to stably adjust the degree of cationization and the molecular weight to the desired values.

5.2. Dissolution of Solid

The method of producing a cationized hyaluronic acid and/or a salt thereof according to this embodiment may further include adding at least one of a sodium salt and a potassium salt to the reaction solution and dissolving a solid produced in the reaction solution after reacting the raw material hyaluronic acid and/or a salt thereof with the cationizing agent. This solid is the main product (cationized hyaluronic acid and/or salt thereof) produced by the cationization reaction.

The concentration of at least one of the sodium salt and the potassium salt in the reaction solution is preferably 5 to 20%. If the concentration of at least one of the sodium salt and the potassium salt is less than 5%, a precipitate may not be obtained in the subsequent step. If the concentration of at least one of the sodium salt and the potassium salt is more than 20%, the sodium salt or the potassium salt may precipitate together with the cationized hyaluronic acid.

5.3. Precipitate

The method of producing a cationized hyaluronic acid and/or a salt thereof according to this embodiment may further include adding an alcohol to the reaction solution in which the solid is dissolved to obtain a precipitate after dissolving the solid in the reaction solution. Examples of the alcohol include methanol and ethanol, with ethanol being preferable. This precipitate is the main product (cationized hyaluronic acid and/or salt thereof) produced by the cationization reaction. Specifically, if the alcohol is added to the reaction solution in which the solid is dissolved to obtain a precipitate (cationized hyaluronic acid and/or salt thereof) after dissolving the solid in the reaction solution, the cationized hyaluronic acid and/or a salt thereof can be separated from the residual cationizing agent and the sodium salt or the potassium salt.

The precipitate may optionally be washed with a solvent (e.g., water-containing alcohol) that dissolves the cationized hyaluronic acid and/or a salt thereof to very little or only a small extent only a small extent. The precipitate is then dried to obtain a purified cationized hyaluronic acid and/or a salt thereof.

The operation of dissolving the solid and the operation of obtaining the precipitate may be repeated a plurality of times.

6. Examples

The invention is further described below by way of examples, comparative examples, and test examples. Note that the invention is not limited to the following examples. Note that the kinematic viscosity was measured by the above-described method.

6.1. Example 1

Preparation of Cationized Hyaluronic Acid According to the Invention

A beaker (volume: 1 L) was charged with 20 g of sodium hyaluronate (manufactured by Q.P. Corporation, average molecular weight: 2,000,000), 20 mL of 5% sodium hydroxide, 180 mL of water-containing ethanol including 80% ethanol, and 30 mL of glycidyltrimethylammonium chloride (GTA (active ingredient: about 80%, water: about 20%)). The components were reacted at 40° C. for one hour while stirring the mixture using a stirrer.

The liquid was then removed by decantation to obtain a solid (including cationized hyaluronic acid).

400 mL of a sodium chloride aqueous solution was then added to the solid to dissolve the solid. After confirming that the solid was completely dissolved, 600 mL of ethanol was added to the solution to precipitate the cationized hyaluronic acid. After removing the liquid by decantation, 500 mL of water-containing ethanol including 80% ethanol was added to the precipitate. The mixture was then stirred for 15 minutes, and the water-containing ethanol was removed by decantation to obtain a further precipitate. This operation was repeated three times to remove the residual cationizing agent (GTA) and sodium chloride from the precipitate.

After further removing the water-containing ethanol by centrifugation, the resulting product was dried at 60° C. for five hours under reduced pressure using a vacuum dryer.

20.5 g of a cationized hyaluronic acid was thus obtained as a white powder. The nitrogen content of the cationized hyaluronic acid was measured. The degree of cationization calculated by the above-mentioned expression was 0.27. The kinematic viscosity (30° C.) of a 0.2% (W/W) aqueous solution of the cationized hyaluronic acid was 13.3 mm²/s.

In Example 1, a large amount of the cationizing agent remained in the cationized hyaluronic acid when the precipitation operation by the addition of ethanol was not performed.

6.2. Example 2

Preparation of Cationized Hyaluronic Acid According to Invention

A beaker (volume: 1 L) was charged with 20 g of sodium hyaluronate (manufactured by Q.P. Corporation, average molecular weight: 1,300,000), 20 mL of 5% sodium hydroxide, 180 mL of water-containing ethanol including 65% ethanol, and 30 mL of glycidyltrimethylammonium chloride (GTA (active ingredient: about 80%, water: about 20%)). The components were reacted at 60° C. for one hour while stirring the mixture using a stirrer.

The liquid was then removed by decantation to obtain a solid (including cationized hyaluronic acid).

400 mL of a sodium chloride aqueous solution was then added to the solid to dissolve the solid. After confirming that the solid was completely dissolved, 600 mL of ethanol was added to the solution to precipitate the cationized hyaluronic acid. After removing the liquid by decantation, 500 mL of water-containing ethanol including 80% ethanol was added to the precipitate. The mixture was then stirred for 15 minutes, and the water-containing ethanol was removed by decantation to obtain a further precipitate. This operation was repeated three times to remove the residual cationizing agent (GTA) and sodium chloride from the precipitate.

After further removing the water-containing ethanol by centrifugation, the resulting product was dried at 60° C. for five hours under reduced pressure using a vacuum dryer.

21.3 g of a cationized hyaluronic acid was thus obtained as a white powder. The nitrogen content of the cationized hyaluronic acid was measured. The degree of cationization calculated by the above-mentioned expression was 0.48. The kinematic viscosity (30° C.) of a 0.2% (W/W) aqueous solution of the cationized hyaluronic acid was 2.3 mm$^2$/s.

6.3. Examples 3 to 20

Preparation of Cationized Hyaluronic Acid

Cationized hyaluronic acids of Examples 3 to 20 were prepared in the same manner as in Example 1, except for using the amount of the cationizing agent, the reaction time, the amount of sodium hydroxide, the water content of the water-containing medium, and the reaction temperature shown in Table 1. The degree of cationization and the kinematic viscosity of each of the cationized hyaluronic acids of Examples 3 to 20 are shown in Table 1. In Table 1, a case where the cationized hyaluronic acid did not bind in the reaction solution was indicated by "S", a case where the cationized hyaluronic acid bound in the reaction solution to a very small extent was indicated by "A", a case where the cationized hyaluronic acid bound in the reaction solution to a small extent was indicated by "B", and a case where the cationized hyaluronic acid bound in the reaction solution to a considerable extent was indicated by "C".

TABLE 1

| Example | Cationizing agent (mL) | Reaction time (hr) | 5% NaOH (mL) | Reaction temperature (° C.) | State of reaction solution | Degree of cationization | Kinematic viscosity (mm$^2$/s) |
|---|---|---|---|---|---|---|---|
| 3 | 20 | 1 | 20 | 60 | S | 0.49 | 2.5 |
| 4 | 30 | 1 | 20 | 60 | S | 0.56 | 2.2 |
| 5 | 40 | 1 | 20 | 60 | S | 0.54 | 2.4 |
| 6 | 60 | 1 | 20 | 60 | A | 0.40 | 7.8 |
| 7 | 80 | 1 | 20 | 60 | C | 0.39 | 8.9 |
| 8 | 30 | 0.1 | 20 | 60 | B | 0.40 | 7.6 |
| 9 | 30 | 0.5 | 20 | 60 | A | 0.46 | 3.8 |
| 10 | 30 | 3 | 20 | 60 | A | 0.44 | 4.4 |
| 11 | 30 | 6 | 20 | 60 | A | 0.41 | 6.2 |
| 12 | 30 | 9 | 20 | 60 | B | 0.43 | 4.3 |
| 13 | 30 | 1 | 10 | 60 | S | 0.58 | 2.1 |
| 14 | 30 | 1 | 30 | 60 | A | 0.38 | 9.2 |
| 15 | 30 | 1 | 40 | 60 | A | 0.25 | 14.2 |
| 16 | 30 | 1 | 20 | 30 | S | 0.21 | 14.8 |
| 17 | 30 | 1 | 20 | 40 | S | 0.25 | 14.1 |
| 18 | 30 | 1 | 20 | 50 | S | 0.33 | 10.5 |
| 19 | 30 | 1 | 20 | 65 | A | 0.54 | 2.3 |
| 20 | 30 | 1 | 20 | 70 | C | 0.48 | 2.7 |

As shown in Table 1, when the amount of the cationizing agent was 80 ml (Example 7), when the reaction time was more than nine hours (Example 12), and when the reaction temperature was higher than 70° C. (Example 20), the state of the reaction solution was poor although cationization proceeded.

Figure 7:
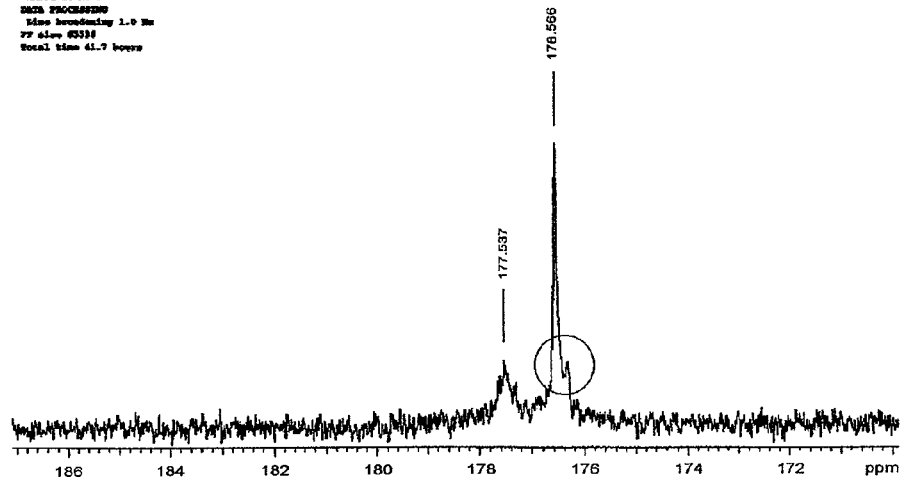
FIG. 7 shows the $^{13}$C NMR spectrum of a cationized hyaluronic acid of Example 18.
Figure 8:
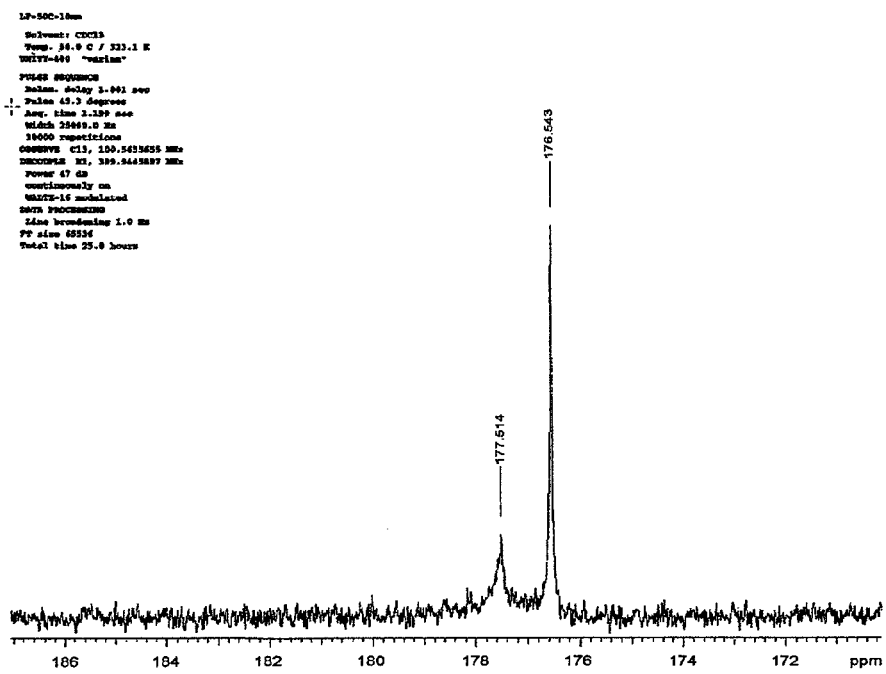
FIG. 8 shows the $^{13}$C NMR spectrum of hyaluronic acid (degree of cationization: 0).

FIG. 7 shows the $^{13}$C NMR spectrum (observation frequency: 100.5 MHz, internal standard substance: DSS (0 ppm), solvent: heavy water) of the cationized hyaluronic acid of Example 18. FIG. 8 shows the $^{13}$C NMR spectrum of hyaluronic acid having a degree of cationization of zero (manufactured by Q.P. Corporation, average molecular weight: 2,000,000) as a comparison.

In the $^{13}$C NMR spectra shown in FIGS. 7 and 8, the peak at 170 to 180 ppm is considered to be a peak that indicates the carbon atom of the —C(=O)O— group of the (cationized) hyaluronic acid.

In the $^{13}$C NMR spectrum of the cationized hyaluronic acid shown in FIG. 7, a peak that was not observed from hyaluronic acid (FIG. 8) was observed at about 176 ppm (encircled in FIG. 7). Therefore, it was confirmed that a quaternary ammonium group-containing group was bonded to the oxygen atom of the (—C(=O)O—) group of the cationized hyaluronic acid of Example 18.

6.4. Comparative Example

Preparation of Cationized Hyaluronic Acid

6.4.1. Comparative Example 1

A beaker (volume: 1 L) was charged with 20 g of sodium hyaluronate (manufactured by Q.P. Corporation, average molecular weight: 1,300,000), 15 mL of 5% sodium hydroxide, 190 mL of water-containing ethanol including 80% ethanol, and 4 mL of glycidyltrimethylammonium chloride (GTA (active ingredient: about 80%, water: about 20%)). The components were reacted at 40° C. for one hour while stirring the mixture using a stirrer.

The liquid was then removed by decantation to obtain a solid (cationized hyaluronic acid).

400 mL of a sodium chloride aqueous solution was then added to the solid to dissolve the solid. After confirming that the solid was completely dissolved, 600 mL of ethanol was added to the solution to precipitate the cationized hyaluronic acid. After removing the liquid by decantation, 500 mL of water-containing ethanol including 80% ethanol was added to the precipitate. The mixture was then stirred for 15 minutes, and the water-containing ethanol was removed by decantation to obtain a further precipitate. This operation was repeated three times to remove the residual cationizing agent (GTA) and sodium chloride from the precipitate.

After further removing the water-containing ethanol by centrifugation, the resulting product was dried at 60° C. for five hours under reduced pressure using a vacuum dryer.

19.5 g of a cationized hyaluronic acid was thus obtained as a white powder. The nitrogen content of the cationized hyaluronic acid was measured. The degree of cationization calculated by the above-mentioned expression was 0.03. The kinematic viscosity (30° C.) of a 0.2% (W/W) aqueous solution of the cationized hyaluronic acid was 20.5 mm$^2$/s.

6.4.2. Comparative Example 2

A beaker (volume: 1 L) was charged with 20 g of sodium hyaluronate (manufactured by Q.P. Corporation, average molecular weight: 1,300,000), 14 mL of 5% sodium hydroxide, 190 mL of water-containing ethanol including 65% ethanol, and 4 mL of glycidyltrimethylammonium chloride (GTA (active ingredient: about 80%, water: about 20%)). The components were reacted at 60° C. for one hour while stirring the mixture using a stirrer.

The liquid was then removed by decantation to obtain a solid (cationized hyaluronic acid).

400 mL of a sodium chloride aqueous solution was then added to the solid to dissolve the solid. After confirming that the solid was completely dissolved, 600 mL of ethanol was added to the solution to precipitate the cationized hyaluronic acid. After removing the liquid by decantation, 500 mL of water-containing ethanol including 80% ethanol was added to the precipitate. The mixture was then stirred for 15 minutes, and the water-containing ethanol was removed by decantation to obtain a further precipitate. This operation was repeated three times to remove the residual cationizing agent (GTA) and sodium chloride from the precipitate.

After further removing the water-containing ethanol by centrifugation, the resulting product was dried at 60° C. for five hours under reduced pressure using a vacuum dryer.

19.7 g of a cationized hyaluronic acid was thus obtained as a white powder. The nitrogen content of the cationized hyaluronic acid was measured. The degree of cationization calculated by the above-mentioned expression was 0.10. The kinematic viscosity (30° C.) of a 0.2% (W/W) aqueous solution of the cationized hyaluronic acid was 17.5 mm$^2$/s.

6.4.3. Comparative Example 3

A beaker (volume: 1 L) was charged with 20 g of sodium hyaluronate (manufactured by Q.P. Corporation, average molecular weight: 1,300,000), 20 mL of 5% sodium hydroxide, 180 mL of water-containing ethanol including 85% ethanol, and 40 mL of glycidyltrimethylammonium chloride (GTA (active ingredient: about 80%, water: about 20%)). The components were reacted at 70° C. for one hour while stirring the mixture using a stirrer. The liquid was then removed by decantation to obtain a solid (cationized hyaluronic acid).

400 mL of a sodium chloride aqueous solution was then added to the solid to dissolve the solid. After confirming that the solid was completely dissolved, 600 mL of ethanol was added to the solution to precipitate the cationized hyaluronic acid. After removing the liquid by decantation, 500 mL of water-containing ethanol including 80% ethanol was added to the precipitate. The mixture was then stirred for 15 minutes, and the water-containing ethanol was removed by decantation to obtain a further precipitate. This operation was repeated three times to remove the residual cationizing agent (GTA) and sodium chloride from the precipitate.

After further removing the water-containing ethanol by centrifugation, the resulting product was dried at 60° C. for five hours under reduced pressure using a vacuum dryer.

17.7 g of a cationized hyaluronic acid was thus obtained as a white powder. The nitrogen content of the cationized hyaluronic acid was measured. The degree of cationization calculated by the above-mentioned expression was 0.82. The kinematic viscosity (30° C.) of a 0.2% (W/W) aqueous solution of the cationized hyaluronic acid was 1.3 mm$^2$/s.

6.4.4. Comparative Example 4

The same operation as in Example 1 was performed, except that the hyaluronic acid was dispersed and dissolved in water instead of water-containing ethanol and cationized. As a result, gelation occurred so that a cationized hyaluronic acid powder could not be obtained.

6.5. Test Example 1

Measurement of Amount of Hyaluronic Acid Adhering to Hair

In this test example, the amount of hyaluronic acid adhering to hair was measured using hyaluronic acids having a given degree of cationization that were prepared in the same manner as in Examples 1 to 20 and Comparative Examples 1 to 3.

6.5.1. Sample

Black human hair (purchased from Beaulax) was used when measuring the amount of hyaluronic acid adhering to hair.

In this test example, a cationized hyaluronic acid having a degree of cationization of 0.03 (Comparative Example 1), 0.10 (Comparative Example 2), 0.21 (Example 16), 0.33 (Example 18), 0.41 (Example 11), 0.56 (Example 4), or 0.82 (Comparative Example 3) was used. As a control, hyaluronic acid having a degree of cationization of zero (manufactured by Q.P. Corporation, average molecular weight: about 1,500,000) was used.

6.5.2. Test Method

6.5.2-1. Preparation of Damaged Hair

Damaged hair was prepared according to the following procedure.

Specifically, black human hair (purchased from Beaulax) was immersed in a 1% aqueous solution of triethanolamine POE (2) lauryl sulfate for one minute.

The hair was washed with water, and dried with a towel. After removing water using paper wiper, the hair was dried using a drier (washing treatment).

The resulting hair was bleached according to the following procedure. A liquid bleach was prepared by mixing a 5% hydrogen peroxide solution and 2.5% aqueous ammonia in a ratio of 1:1. The hair was immersed in the liquid bleach at 30° C. for 20 minutes (bleaching treatment).

The washing treatment and the bleaching treatment were then repeated ten times. Damaged hair was thus obtained.

6.5.2-2. Adhesion of Hyaluronic Acid to Damaged Hair

A sample aqueous solution having a concentration of 0.005% was prepared using each sample (two specimens were prepared for each sample). About 1 mL of the sample aqueous solution was removed and filtered through a membrane filter (pore size: 0.45 micrometers) to obtain a pretreatment HPLC measurement sample.

10 mL of the sample aqueous solution was put in a lidded test tube using a transfer pipette. 1 g of the damaged hair prepared by the above procedure was weighed, and immersed in the sample aqueous solution in the test tube placed in a thermostat bath for 10 minutes.

About 1 mL of the sample aqueous solution was removed from the test tube in which the hair was immersed, and filtered through a membrane filter (pore size: 0.45 micrometers) to obtain a post-treatment HPLC measurement sample.

6.5.2-3. HPLC Measurement (i) HPLC Measurement Principle

Hair is negatively charged while the cationized hyaluronic acid is positively charged. Therefore, since the cationized hyaluronic acid is electrically drawn toward and adheres to the hair, the concentration of the cationized hyaluronic acid in the sample aqueous solution decreases. A decrease in concentration is measured by HPLC, and the amount of hyaluronic acid adhering to the hair is calculated by the following expression.

Amount (mg) of hyaluronic acid adhering to 1 g of hair=
[(sample concentration before treatment (%)–
sample concentration after treatment (%))×$10^2$]/
weight of hair (g)

(ii) HPLC Analysis Conditions
Column: TSK guard column PWXL+TSK gel GMPW×2
Column temperature: 40° C.
Measurement wavelength: 210 nm
Flow rate: 0.8 mL/min
Sample injection amount: 100 microliters
Analysis time: 40 minutes
Mobile phase: 0.003 mol/L phosphate buffer-0.15 mol/L NaCl (pH: 7.0)
Photodiode array: "996 Photodiode Array" manufactured by Nihon Waters Inc.
HPLC system: "2690 Separation Module" manufactured by Nihon Waters Inc.

6.5.2-4. Measurement of Amount of Hyaluronic Acid Adhering to Hair
(i) Calibration Curve A calibration curve indicating the correlation between the peak area and the sample concentration was calculated from the sample aqueous solution having a known concentration. The calibration curve was created corresponding to each sample.

(ii) Calculation of Sample Concentration in Sample Aqueous Solution

The sample concentration in the sample aqueous solution was calculated from the calibration curve obtained in (i) to calculate the amount of the sample in the sample aqueous solution before and after the treatment. Note that the amount of the sample in 10 mL of the sample aqueous solution in the test tube in which the hair was immersed was first calculated, and the amount of the sample adhering to 1 g of the hair was then calculated.

6.5.3. Test Results 6.5.3-1. Amount of Hyaluronic Acid Adhering to Hair

FIG. 1 shows the HPLC measurement results. As shown in FIG. 1, the amount of hyaluronic acid adhering to the hair increased in proportion to the degree of cationization of the cationized hyaluronic acid (HA). When the degree of cationization of the cationized hyaluronic acid was less than 0.15, the amount of hyaluronic acid adhering to the hair was relatively small. The reason therefor is considered to be as follows. Specifically, since the cationized hyaluronic acid was drawn toward the hair to only a small extent when the degree of cationization of the cationized hyaluronic acid was less than 0.15, the cationized hyaluronic acid did not sufficiently adhere to the hair.

6.6. Test Example 2

Hair Sensory Evaluation 6.6.1. Preparation of Damaged Hair

Damaged hair was prepared according to the following procedure.

Black human hair (purchased from Beaulax) was immersed in a 1% aqueous solution of triethanolamine POE (2) lauryl sulfate for one minute.

The hair was washed with water, and dried with a towel. After removing water using paper wiper, the hair was dried using a drier (washing treatment).

The resulting hair was bleached according to the following procedure. A liquid bleach was prepared by mixing a 5% hydrogen peroxide solution and 2.5% aqueous ammonia in a ratio of 1:1. The hair was immersed in the liquid bleach at 30° C. for 20 minutes (bleaching treatment).

The washing treatment and the bleaching treatment were then repeated ten times. Damaged hair was thus obtained.

6.6.2. Evaluation method

Leave-In Hair Cosmetic Preparation)

In this test example, a cationized hyaluronic acid having a degree of cationization of 0.03 (Comparative Example 1), 0.10 (Comparative Example 2), 0.21 (Example 16), 0.33 (Example 18), 0.41 (Example 11), 0.56 (Example 4), or 0.82 (Comparative Example 3) was used. As a control, hyaluronic acid having a degree of cationization of zero (manufactured by Q.P. Corporation, average molecular weight: about 1,500,000) was used.

(i) A 1% sample aqueous solution (0.15 g/15 mL, test tube) was prepared using the cationized hyaluronic acid or hyaluronic acid having a degree of cationization of zero.

(ii) A bundle of the damaged hair prepared in 6.6.1. was immersed in the 1% sample aqueous solution. After allowing the 1% sample aqueous solution to stand at 25° C. for five minutes, the hair bundle was removed from the sample solution, and dried using a dryer.

(iii) The feel of the hair bundle after the treatment was evaluated by five adult men and women. A blind evaluation was repeated twice on each sample (ten times in total (No. 1 to No. 10)).

The hair bundle was lightly taken between the thumb and the index finger, and whether or not the feel when moving the fingers from the root to the tip was better than that of the control (treated with distilled water) was evaluated. The overall evaluation was based on moisturization, smoothness, dryness, and roughness. Note that the damaged hair used in this test example had dryness near the tip. Table 2 shows the evaluation system.

TABLE 2

| Evaluation of leave-in hair cosmetic preparation | |
|---|---|
| Points | Feel of hair bundle |
| 3 | Moisturization and smoothness are excellent as compared with control |
| 2 | Moisturization and smoothness are good as compared with control |
| 1 | Moisturization and smoothness are better than control to some extent |
| 0 | Equal to control |
| −1 | Dry and rough to some extent as compared with control |

6.6.3. Evaluation Method

Rinse-Out Hair Cosmetic Preparation

In this test example, an evaluation sample (cationized hyaluronic acid or sodium hyaluronate) similar to that used in 6.6.2. was used.

(i) A 1% sample aqueous solution (0.15 g/15 mL, test tube) was prepared using the cationized hyaluronic acid or hyaluronic acid having a degree of cationization of zero.

(ii) A bundle of the damaged hair prepared in 6.6.1. was immersed in the 1% sample aqueous solution. The 1% sample aqueous solution was allowed to stand at 40° C. (thermostat bath) for five minutes. The hair bundle was removed from the 1% sample aqueous solution, washed with running water, dried with a towel, and dried using a drier. The step (ii) was repeated three times.

(iii) The hair bundle was evaluated in the same manner as in (iii) in 6.6.2. Table 3 shows the evaluation system.

TABLE 3

Evaluation of rinse-out hair cosmetic preparation

| Points | Feel of hair bundle |
|---|---|
| 3 | Moisturization and smoothness are excellent as compared with control |
| 2 | Moisturization and smoothness are good as compared with control |

TABLE 3-continued

Evaluation of rinse-out hair cosmetic preparation

| Points | Feel of hair bundle |
|---|---|
| 1 | Moisturization and smoothness are better than control to some extent |
| 0 | Equal to control |
| −1 | Dry and rough to some extent as compared with control |

6.6.4. Evaluation Results

The evaluation results are shown in Tables 4 and 5. The evaluation standard was as follows.
S: 2 points or more (average)
A: 1 point or more and less than 2 points (average)
B: 0 points or more and less than 1 point (average)
C: Less than 0 points (average)

TABLE 4

Evaluation results for leave-in hair cosmetic preparation

| Degree of cationization | No. 1 | No. 2 | No. 3 | No. 4 | No. 5 | No. 6 | No. 7 | No. 8 | No. 9 | No. 10 | Total | Average | Evaluation |
|---|---|---|---|---|---|---|---|---|---|---|---|---|---|
| 0 | 1 | 2 | 0 | 1 | 1 | 0 | 1 | 1 | 0 | 1 | 8 | 0.8 | B |
| 0.03 | 0 | 2 | 1 | 1 | 1 | 1 | 0 | 1 | 0 | 2 | 9 | 0.9 | B |
| 0.10 | 0 | 2 | 1 | 2 | 2 | 2 | 0 | 2 | 1 | 2 | 14 | 1.4 | A |
| 0.21 | 2 | 3 | 2 | 3 | 3 | 3 | 3 | 3 | 2 | 3 | 27 | 2.7 | S |
| 0.33 | 2 | 3 | 3 | 3 | 3 | 3 | 3 | 3 | 2 | 3 | 28 | 2.8 | S |
| 0.41 | 2 | 3 | 3 | 3 | 3 | 3 | 3 | 2 | 2 | 3 | 27 | 2.7 | S |
| 0.56 | 2 | 2 | 3 | 2 | 2 | 3 | 2 | 3 | 2 | 2 | 23 | 2.3 | S |
| 0.82 | 1 | 2 | 2 | 1 | 2 | 2 | 2 | 2 | 2 | 2 | 18 | 1.8 | A |

In Table 4, when using the samples evaluated as "S" (cationized hyaluronic acids having a degree of cationization of 0.21 (Example 16), 0.33 (Example 18), 0.41 (Example 11), or 0.56 (Example 4)), excellent moisturization and smoothness were obtained as compared with the case of using the control. Moreover, the hair was well-bundled. In particular, when using the samples having a degree of cationization of 0.21 (Example 16), 0.33 (Example 18), or 0.41 (Example 11), 90% or more of the estimators felt excellent moisturization and smoothness. On the other hand, when using the samples having a degree of cationization of 0 (control), 0.03 (Comparative Example 1), or 0.10 (Comparative Example 2), moisturization was not obtained (dryness occurred), and the hair was not well-bundled. When using the sample having a degree of cationization of 0.82 (Comparative Example 3), sufficient moisturization and smoothness were not obtained and roughness occurred. Therefore, it was confirmed that the cationized hyaluronic acid according to the invention having a degree of cationization of 0.15 to 0.4 is suitable for use as a leave-in hair cosmetic preparation.

TABLE 5

Evaluation results for rinse-out hair cosmetic preparation

| Degree of cationization | No. 1 | No. 2 | No. 3 | No. 4 | No. 5 | No. 6 | No. 7 | No. 8 | No. 9 | No. 10 | Total | Average | Evaluation |
|---|---|---|---|---|---|---|---|---|---|---|---|---|---|
| 0 | 1 | 2 | 1 | 1 | 1 | 0 | 1 | 1 | 0 | 1 | 9 | 0.9 | B |
| 0.03 | 0 | 2 | 1 | 1 | 0 | 1 | 0 | 1 | 0 | 1 | 7 | 0.7 | B |
| 0.10 | 1 | 2 | 1 | 1 | 1 | 1 | 0 | 2 | 1 | 2 | 12 | 1.2 | A |
| 0.21 | 2 | 3 | 3 | 3 | 2 | 1 | 2 | 2 | 1 | 2 | 21 | 2.1 | S |
| 0.33 | 3 | 3 | 3 | 2 | 1 | 3 | 3 | 3 | 2 | 3 | 26 | 2.6 | S |
| 0.41 | 3 | 3 | 3 | 3 | 2 | 2 | 3 | 3 | 3 | 3 | 28 | 2.8 | S |
| 0.56 | 3 | 3 | 3 | 2 | 3 | 2 | 3 | 3 | 3 | 3 | 28 | 2.8 | S |
| 0.82 | 2 | 2 | 3 | 2 | 2 | 1 | 2 | 2 | 1 | 2 | 19 | 1.9 | A |

In Table 5, when using the samples evaluated as "S" (cationized hyaluronic acids having a degree of cationization of 0.21 (Example 16), 0.33 (Example 18), 0.41 (Example 11), or 0.56 (Example 4)), excellent moisturization and smoothness were obtained as compared with the case of using the control. Moreover, the hair was well-bundled. In particular, when using the samples having a degree of cationization of 0.41 (Example 11) or 0.56 (Example 4), 90% or more of the estimators felt excellent moisturization and smoothness. On the other hand, when using the samples having a degree of cationization of 0 (control), 0.03 (Comparative Example 1), or 0.10 (Comparative Example 2), moisturization was not obtained (dryness occurred), and the hair was not well-bundled. When using the sample having a degree of cationization of 0.82 (Comparative Example 3), sufficient moisturization and smoothness were not obtained and roughness occurred. Therefore, it was confirmed that the cationized hyaluronic acid according to the invention having a degree of cationization of 0.4 to 0.6 is suitable for use as a rinse-out hair cosmetic preparation.

From the above results, it was confirmed that dry damaged hair can be moisturized and provided with smoothness by utilizing the cationized hyaluronic acid according to the invention having a degree of cationization of 0.15 to 0.6.

6.7. Test Example 3

Scanning Electron Micrograph of Hair

In this test example, the cationized hyaluronic acid having a degree of cationization of 0.33 (Example 18) was used as an evaluation sample, and distilled water was used as a control. Damaged hair was treated in the same manner as in (i) and (ii) in 6.6.3.

Figure 2:
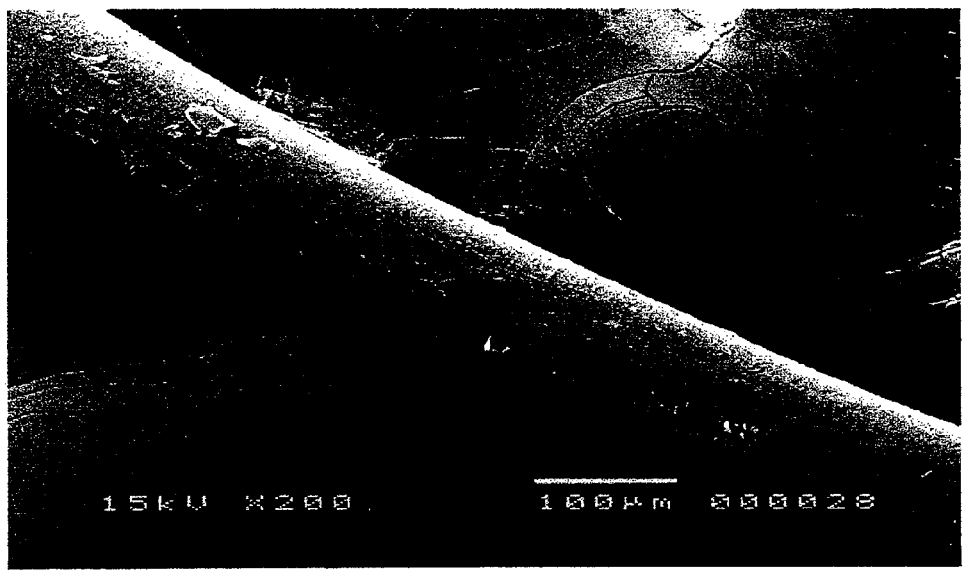
FIG. 2 shows a scanning electron micrograph (magnification: 200) of hair treated using a cationized hyaluronic acid having a degree of cationization of 0.33 (Example 18) in Test Example 3.
Figure 3:
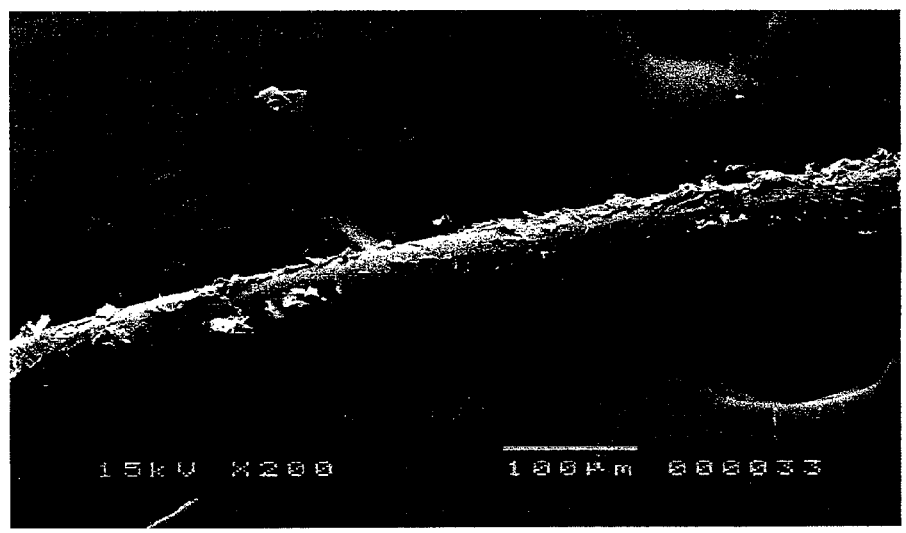
FIG. 3 shows a scanning electron micrograph (magnification: 200) of hair treated using distilled water in Test Example 3.
Figure 4:
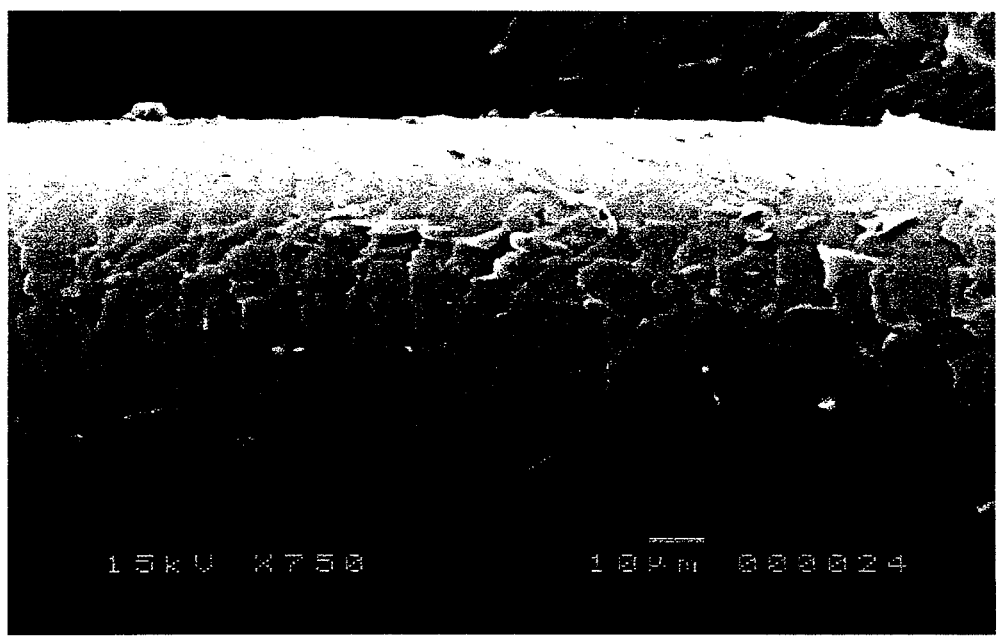
FIG. 4 shows a scanning electron micrograph (magnification: 750) of hair treated using a cationized hyaluronic acid having a degree of cationization of 0.33 (Example 18).

Scanning electron micrographs of the hair treated using the cationized hyaluronic acid having a degree of cationization of 0.33 (Example 18) are shown in FIG. 2 (magnification: 200) and FIG. 4 (magnification: 750). Scanning electron micrographs of the hair treated using distilled water are shown in FIG. 3 (magnification: 200) and FIG. 5 (magnification: 750).

Figure 5:
FIG. 5 shows a scanning electron micrograph (magnification: 750) of hair treated using distilled water in Test Example 3.

In FIGS. 2 and 4, detachment of cuticles of the hair occurs to only a small extent, and the surface of the hair is the relatively smooth. In FIGS. 3 and 5, cuticles of the hair are irregularly separated, and ruggedness occurs on the surface of the hair.

The damaged hair is normally rough to the touch. On the other hand, the damaged hair treated using the cationized hyaluronic acid is smooth to the touch. From the comparison between the photographs shown in FIGS. 2 to 5, it is considered that the cuticle state affects the feel of the hair. Specifically, the damaged hair is rough to the touch due to separation of cuticles. On the other hand, the damaged hair treated using the cationized hyaluronic acid is smooth to the touch since separation of the cuticles is repaired.

The mechanism by which hair that is smooth to the touch is obtained using the cationized hyaluronic acid is thought to be as described in the following (i) and (ii).
(i) The cationized hyaluronic acid enters the space between the separated cuticles of the hair. Since the cationized hyaluronic acid is positively charged as compared with uncationized hyaluronic acid, the cationized hyaluronic acid promptly enters the space between the cuticles on the surface of the hair that is normally negatively charged as compared with uncationized hyaluronic acid.
(ii) The separated cuticles are drawn toward the cuticle in the lower layer due to a hydrogen bond between the cationized hyaluronic acids so that the cuticles adhere to each other. As a result, the cuticle layer becomes smooth so that the hair becomes smooth to the touch.

6.8. Test Example 4

Measurement of Amount of Hyaluronic Acid Adhering to Skin and Sensory Evaluation In this test example, the amount of hyaluronic acid adhering to skin was measured using hyaluronic acids having a given degree of cationization that were prepared in the same manner as in Examples 1 to 20.

6.8.1. Sample

In this test example, a cationized hyaluronic acid having a degree of cationization of 0.03 (Comparative Example 1), 0.21 (Example 16), 0.33 (Example 18), 0.56 (Example 4), or 0.82 (Comparative Example 3) was used. As a control, hyaluronic acid having a degree of cationization of zero (manufactured by Q.P. Corporation, average molecular weight: about 600,000) was used.

6.8.2. Test Method

6.8.2-1. Preparation of Sample Aqueous Solution

A sample aqueous solution containing 1% of hyaluronic acid was prepared. 6.8.2-2. Application of hyaluronic acid to skin 0.5 mL of the sample aqueous solution was placed on the forearm within the range of 7×7 cm, and was spread with the finger so that the sample aqueous solution was uniformly applied. After three minutes has elapsed, the applied area was washed with running water for 10 seconds at a flow rate of 3 L/min, and was allowed to dry.

6.8.2-3. Sensory Evaluation

Moisturization and smoothness after applying the sample aqueous solution to the skin were evaluated by five adult men and women (21 to 50 years old) who suffered from rough skin (e.g., dry skin). A blind evaluation was repeated twice on each sample (ten times in total. (No. 1 to No. 10)).

Whether or not the feel of the skin when touching the skin with the finger was better than that of the control (distilled water) was evaluated. The overall evaluation was based on moisturization, smoothness, and dryness. Table 6 shows the evaluation system.

TABLE 6

| Points | Feel of skin |
| --- | --- |
| 3 | Moisturization and smoothness are excellent as compared with control |
| 2 | Moisturization and smoothness are good as compared with control |
| 1 | Moisturization and smoothness are better than control to some extent |
| 0 | Equal to control |
| −1 | Dry to some extent as compared with control |

6.8.2-4. Removal of Hyaluronic Acid from Skin

An adhesive tape was attached to the applied area and slowly removed so that hyaluronic acid adhered to the adhesive tape. The adhesive tape was then placed in a centrifuge tube (50 mL), and the hyaluronic acid was separated from the adhesive tape using 20 mL of a chloroform/methanol (1:1) mixture. After the addition of an equal amount of distilled water, the mixture was stirred and centrifuged to collect the aqueous phase. After distilling the aqueous phase under reduced pressure, 1 mL of distilled water was added to dissolve the aqueous phase. The solution was then filtered through a membrane filter (pore size: 0.45 micrometers) to obtain an HPLC measurement sample.

6.8.2-5. HPLC Analysis Conditions (i) HPLC measurement principle
Column: TSK guard column PWXL+TSK gel GMPW×2
Column temperature: 40° C.
Measurement wavelength: 210 nm
Flow rate: 0.8 mL/min
Sample injection amount: 100 microliters
Analysis time: 40 minutes
Mobile phase: 0.003 mol/L phosphate buffer-0.15 mol/L NaCl (pH: 7.0)
Photodiode array: "996 Photodiode Array" manufactured by Nihon Waters K.K.
HPLC system: "2690 Separation Module" manufactured by Nihon Waters K.K.

6.8.2-6. Calculation of Amount of Hyaluronic Acid Adhering to Skin (i) Calibration Curve A calibration curve indicating the correlation between the peak area and the amount of hyaluronic acid in the HPLC measurement sample was calculated from the sample aqueous solution having a known concentration. The calibration curve was created corresponding to each sample.

(ii) Calculation of Sample Concentration in Sample Aqueous Solution

The amount of hyaluronic acid in the HPLC measurement sample was calculated from the calibration curve obtained in (i).

6.8.3. Test Results

6.8.3-1. Sensory Evaluation

The evaluation results are shown in Table 7. The evaluation standard employed in Table 7 was as follows.
S: 2 points or more (average)
A: 1 point or more and less than 2 points (average)
B: 0 points or more and less than 1 point (average)
C: Less than 0 points (average)

In Table 7, when using the samples evaluated as "S" (cationized hyaluronic acids having a degree of cationization of 0.21 (Example 16), 0.33 (Example 18), or 0.56 (Example 4), the skin was smooth as compared with the case of using the control. Specifically, an excellent skin moisturization effect was obtained. In particular, when using the samples having a degree of cationization of 0.33 (Example 18) or 0.56 (Example 4), 80% or more of the estimators felt excellent moisturization and smoothness. On the other hand, when using the samples having a degree of cationization of 0 (control) or 0.03 (Comparative Example 1), the sample did not provide a sense of adhering to the skin, and moisturization and smoothness of the skin were not obtained. When using the sample having a degree of cationization of 0.82 (Comparative Example 3), sufficient moisturization and smoothness were not obtained although the sample provided a sense of adhering to the skin.

From the above results, it was confirmed that skin can be moisturized and provided with smoothness by utilizing the cationized hyaluronic acid according to the invention having a degree of cationization of 0.15 to 0.6.

6.8.3-2. Amount of Hyaluronic Acid Adhering to Skin

Figure 6:
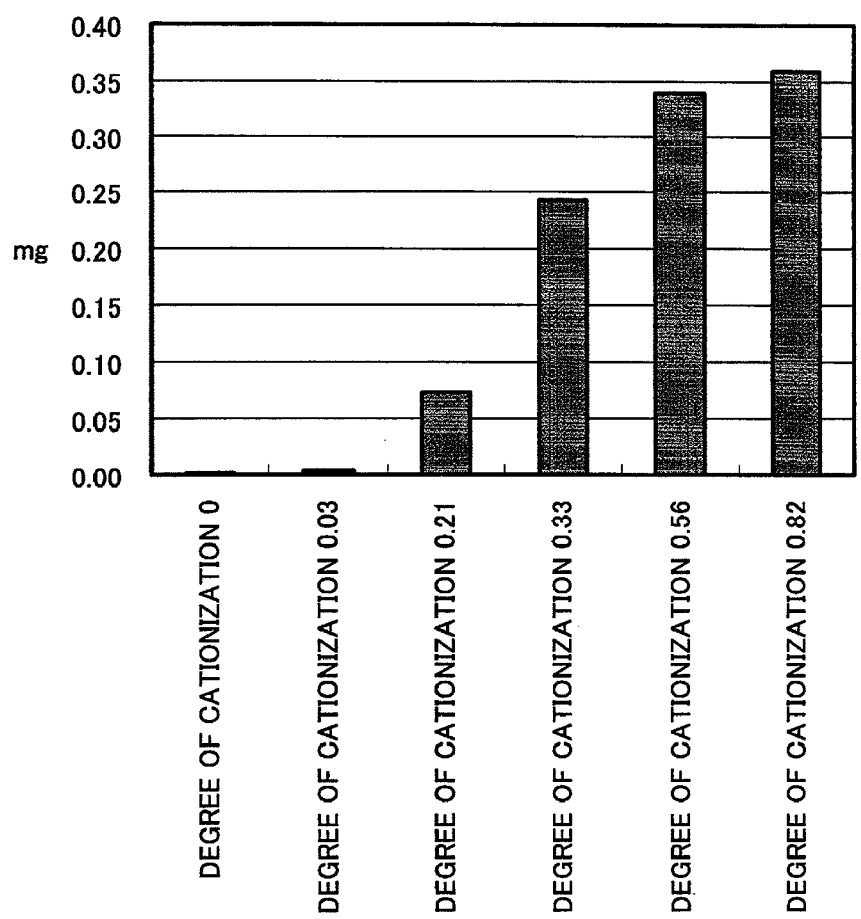
FIG. 6 is a graph showing the amount of each sample adhering to skin determined in Test Example 4.

FIG. 6 shows the HPLC measurement results. As shown in FIG. 6, the amount of hyaluronic acid adhering to the skin increased in proportion to the degree of cationization of the cationized hyaluronic acid (HA). When the degree of cationization of the cationized hyaluronic acid was less than 0.15, the amount of hyaluronic acid adhering to the skin was relatively small. The reason therefor is considered to be as follows. Specifically, since the cationized hyaluronic acid was drawn toward the skin to only a small extent when the degree of cationization of the cationized hyaluronic acid was less than 0.15, the cationized hyaluronic acid did not sufficiently adhere to the skin.

6.9. Test Example 6

Preparation of Cosmetic Preparation

In this test example, a rinse-out hair cosmetic preparation (shampoo) containing the cationized hyaluronic acid obtained in Example 1 was prepared according to the following formulation.
Cationized hyaluronic acid (Example 1): 0.1% Sodium polyoxyethylene (2) lauryl ether sulfate: 11.0% Palm oil fatty acid amide propyl betaine: 4.0% Palm oil fatty acid monoethanolamide: 2.0% Sodium edetate: 0.1% Sodium benzoate: 0.2% Essence, dye, and preservative: proper quantities Purified water: balance According to this test example, shampoo that exhibited excellent adhesion to hair was obtained by incorporating the cationized hyaluronic acid obtained in Example 1.

TABLE 7

| Degree of cationization | No. 1 | No. 2 | No. 3 | No. 4 | No. 5 | No. 6 | No. 7 | No. 8 | No. 9 | No. 10 | Total | Average | Evaluation |
|---|---|---|---|---|---|---|---|---|---|---|---|---|---|
| 0 | 0 | 0 | 1 | 0 | 0 | 0 | 0 | 0 | 0 | 1 | 2 | 0.2 | B |
| 0.03 | 0 | 0 | 1 | 1 | 1 | 0 | 0 | 0 | 1 | 0 | 4 | 0.4 | B |
| 0.21 | 2 | 1 | 2 | 3 | 1 | 2 | 2 | 2 | 2 | 3 | 20 | 2.0 | S |
| 0.33 | 3 | 2 | 2 | 3 | 2 | 3 | 2 | 3 | 2 | 2 | 24 | 2.4 | S |
| 0.56 | 3 | 2 | 2 | 3 | 1 | 3 | 2 | 2 | 3 | 3 | 24 | 2.4 | S |
| 0.82 | 3 | 1 | 1 | 2 | 2 | 2 | 2 | 1 | 2 | 2 | 18 | 1.8 | A |

6.10. Test Example 7

Preparation of Cosmetic Preparation

In this test example, a rinse-out hair cosmetic preparation (rinse) containing the cationized hyaluronic acid obtained in Example 2 was prepared according to the following formulation.
Cationized hyaluronic acid (Example 2): 0.3%
Cetostearyl alcohol: 2.0%
POE (5) cetyl ether: 1.0%
Glycerol: 3.0%
1,3-Butylene glycol: 5.0%
Silicone oil: 3.0%
Wheat hydrolyzate: 1.0%
Hydroxystearic acid: 0.5%
Cetyl 2-ethylhexanoate: 1.0%
Distearyldimethylammonium chloride: 0.2%
Dimethylaminopropylamide behenate: 0.5%
Essence, dye, and preservative: proper quantities
Purified water: balance According to this test example, rinse that exhibited excellent adhesion to hair was obtained by incorporating the cationized hyaluronic acid obtained in Example 2.

6.11. Test Example 8

Preparation of Cosmetic Preparation

In this test example, a rinse-out hair cosmetic preparation (rinse-in-shampoo) containing the cationized hyaluronic acid obtained in Example 1 was prepared according to the following formulation.
Cationized hyaluronic acid (Example 1): 0.2%
Imidazolium betaine amphoteric surfactant: 16.0%
Palm oil fatty acid diethanolamide: 4.0%
Stearyltrimethylammonium chloride: 2.0%
Sodium N-lauroyl-N-methyl-beta-alanine: 1.0%
Silicone derivative: 1.0%
Polyoxyethylene alkyl polyamine: 1.0%
Essence, dye, and pH adjusting agent: proper quantities
Purified water: balance According to this test example, a rinse-in-shampoo that exhibited excellent adhesion to hair was obtained by incorporating the cationized hyaluronic acid obtained in Example 1.

6.12. Test Example 9

Preparation of Cosmetic Preparation

In this test example, a rinse-out hair cosmetic preparation (hair conditioner) containing the cationized hyaluronic acid obtained in Example 2 was prepared according to the following formulation.
Cationized hyaluronic acid (Example 2): 0.5%
Stearyl alcohol: 4.0%
Cetanol: 1.5%
Hydroxyethyl urea: 1.0%
Dimethicone: 2.0%
Hydrolyzed silk: 1.0%
1,3-Butylene glycol: 1.0%
Glycerol: 3.0%
Cetyl 2-ethylhexanoate: 2.0%
Isocetyl myristate: 0.4%
L-Arginine: 0.1%
Polyoxyethylene (4) stearyl ether: 1.0%
Dimethylaminopropylamide stearate: 1.5%
Sodium benzoate: 0.3%
Essence and preservative: proper quantities
Purified water: balance According to this test example, a hair conditioner that exhibited excellent adhesion to hair was obtained by incorporating the cationized hyaluronic acid obtained in Example 2.

6.13. Test Example 10

Preparation of Cosmetic Preparation

In this test example, a rinse-out hair cosmetic preparation (hair pack) containing the cationized hyaluronic acid obtained in Example 2 was prepared according to the following formulation.
Cationized hyaluronic acid (Example 2): 1.0%
Cetyl alcohol; 2.0%
Stearyl alcohol: 2.0%
Stearic acid hydrogenated castor oil: 2.0%
Isopropyl myristate: 1.0%
Stearyltrimethylammonium bromide: 3.0%
Stearyldimethylammonium chloride: 2.0%
1,3-Butylene glycol: 10.0%
Essence and preservative: proper quantities
Purified water: balance According to this test example, a hair pack that exhibited excellent adhesion to hair was obtained by incorporating the cationized hyaluronic acid obtained in Example 2.

6.14. Test Example 11

Preparation of Cosmetic Preparation

In this test example, a leave-in hair cosmetic preparation (undiluted hair conditioner) containing the cationized hyaluronic acid obtained in Example 1 was prepared according to the following formulation.
Cationized hyaluronic acid (Example 1): 2.0%
Preservative: proper quantity
Purified water: balance According to this test example, an undiluted hair conditioner that exhibited excellent adhesion to hair was obtained by incorporating the cationized hyaluronic acid obtained in Example 1.

6.15. Test Example 12

Preparation of Cosmetic Preparation

In this test example, a rinse-out hair cosmetic preparation (hair pack) containing the cationized hyaluronic acid obtained in Example 2 was prepared according to the following formulation.
Cationized hyaluronic acid (Example 2): 1.0% Cetyl alcohol; 2.0% Stearyl alcohol: 2.0% Stearic acid hydrogenated castor oil: 2.0% Isopropyl myristate: 1.0% Stearyltrimethylammonium bromide: 3.0% Distearyldimethylammonium chloride: 2.0% 1,3-Butylene glycol: 10.0% Essence and preservative: proper quantities Purified water: balance According to this test example, hair cream that exhibited excellent adhesion to hair was obtained by incorporating the cationized hyaluronic acid obtained in Example 1.

6.16. Test Example 13

Preparation of Cosmetic Preparation

In this test example, a leave-in hair cosmetic preparation (hair wax) containing the cationized hyaluronic acid obtained in Example 1 was prepared according to the following formulation.
Cationized hyaluronic acid (Example 1): 0.5%
PEG-20 glyceryl isostearate: 3.0%
Glyceryl stearate: 2.0%
Microcrystalline wax: 4.0%
Carnauba wax: 3.0%
Behenyl alcohol: 3.0%
Stearic acid: 1.0%
Mineral oil: 2.0%
Hydrogenated polyisobutene: 2.0%
Phenyltrimethicone: 3.0%
Dimethicone: 1.0%
Propylparaben: 0.1%
PVP: 1.0%
Propylene glycol: 5.0%
Preservative: proper quantity
Purified water: balance According to this test example, hair wax that exhibited excellent adhesion to hair was obtained by incorporating the cationized hyaluronic acid obtained in Example 1.

6.17. Test Example 14

Preparation of Cosmetic Preparation

In this test example, a leave-in hair cosmetic preparation (hair gel) containing the cationized hyaluronic acid obtained in Example 2 was prepared according to the following formulation.
Cationized hyaluronic acid (Example 2): 1.0%
Polyvinylpyrrolidone: 2.0%
Glycerol: 5.0%
Ethanol: 20.0%
Polyoxyethylene octyl dodecyl ether: 1.0%
Sodium hydroxide: proper quantity
Essence and chelating agent: proper quantities
Purified water: balance According to this test example, hair gel that exhibited excellent adhesion to hair was obtained by incorporating the cationized hyaluronic acid obtained in Example 2.

6.18. Test Example 15

Preparation of Cosmetic Preparation

In this test example, a leave-in hair cosmetic preparation (hair mousse) containing the cationized hyaluronic acid obtained in Example 2 was prepared according to the following formulation.
Cationized hyaluronic acid (Example 2): 3.0%
Polyoxyethylene hydrogenated castor oil: proper quantity
Silicone oil: 5.0%
Dipropylene glycol: 7.0%
Ethanol: 15.0%
Essence and preservative: proper quantities
Purified water: balance According to this test example, hair mousse that exhibited excellent adhesion to hair was obtained by incorporating the cationized hyaluronic acid obtained in Example 2.

6.19. Test Example 16

Preparation of Cosmetic Preparation

In this test example, a leave-in hair cosmetic preparation (hair lotion) containing the cationized hyaluronic acid obtained in Example 1 was prepared according to the following formulation.
Cationized hyaluronic acid (Example 1): 1.0%
Polyvinylpyrrolidone: 4.0%
Ethanol: 30.0%
Silicone derivative: 0.5%
Glycerol: 2.0%
Essence and preservative: proper quantities
Purified water: balance According to this test example, hair lotion that exhibited excellent adhesion to hair was obtained by incorporating the cationized hyaluronic acid obtained in Example 1.

6.20. Test Example 17

Preparation of Cosmetic Preparation

In this test example, a leave-in hair cosmetic preparation (hair color pretreatment liquid) containing the cationized hyaluronic acid obtained in Example 1 was prepared according to the following formulation.
Cationized hyaluronic acid (Example 1): 0.5%
Imidazolinium betaine: 1.0%
Keratin hydrolyzate: 0.5%
Glycine: 0.5%
POE lauryl ether: 0.5%
Purified water: balance According to this test example, a hair color pretreatment liquid that exhibited excellent adhesion to hair was obtained by incorporating the cationized hyaluronic acid obtained in Example 1.

6.21. Test Example 18

Preparation of Cosmetic Preparation

In this test example, a leave-in hair cosmetic preparation (coloring agent) containing the cationized hyaluronic acid obtained in Example 1 was prepared according to the following formulation.
Cationized hyaluronic acid (Example 1): 0.5%
Benzyl alcohol: 8.0%
Citric acid: 1.0%
Ethanol: 15.0%
Black No. 401: 0.05%
Brown No. 201: 0.13%
Sodium hydroxide: proper quantity
Purified water: balance According to this test example, a coloring agent that exhibited excellent adhesion to hair was obtained by incorporating the cationized hyaluronic acid obtained in Example 1.

6.22. Test Example 19

Preparation of Cosmetic Preparation

In this test example, a leave-in hair cosmetic preparation (permanent secondary solution) containing the cationized hyaluronic acid obtained in Example 1 was prepared according to the following formulation.
Cationized hyaluronic acid (Example 1): 0.5%
Sodium bromate: 5.0%
Silicone emulsion: 1.0%
Citric acid: 0.1%
Sodium citrate: 0.5%
Purified water: balance According to this test example, a permanent secondary solution that exhibited excellent adhesion to hair was obtained by incorporating the cationized hyaluronic acid obtained in Example 1.

6.23. Test Example 20

Preparation of Cosmetic Preparation

In this test example, a leave-in hair cosmetic preparation (aqueous mascara) containing the cationized hyaluronic acid obtained in Example 1 was prepared according to the following formulation.
Cationized hyaluronic acid (Example 1): 0.5%
Isopropyl alcohol: 5.0%
1,3-Butylene glycol: 5.0%
Potassium hydroxide: 0.1%
Zinc oxide: 0.1%
Pigment: 2.0%
Dextrin: 14.0%
Essence and preservative: proper quantities
Purified water: balance According to this test example, aqueous mascara that exhibited excellent adhesion to hair was obtained by incorporating the cationized hyaluronic acid obtained in Example 1.

6.24. Test Example 21

Preparation of Cosmetic Preparation

In this test example, a facial wash containing the cationized hyaluronic acid obtained in Example 1 was prepared according to the following formulation.
Cationized hyaluronic acid (Example 1): 1.0%
Glycerol: 15.0%
Polyethylene glycol 400: 5.0%
Lauric acid: 5.0%
Myristic acid: 8.0%
Palmitic acid: 9.0%
Stearic acid: 18.0%
Sodium lauroylmethyltaurine: 4.0%
Fatty acid monoglyceride: 1.5%
Polyglyceryl monolaurate: 1.0%
Potassium hydroxide: 1.0%
Linalool: proper quantity
Purified water: balance According to this test example, a facial wash that exhibited excellent adhesion to skin was obtained by incorporating the cationized hyaluronic acid obtained in Example 1.

6.25. Test Example 22

Preparation of Cosmetic Preparation

In this test example, toilet lotion containing the cationized hyaluronic acid obtained in Example 1 was prepared according to the following formulation.
Cationized hyaluronic acid (Example 1): 0.2%
Sodium hyaluronate: 0.2%
Hydrolyzed hyaluronic acid: 0.2%
Cetyl octanoate: 0.3%
Octyl methoxycinnamate: 0.15%
Tocopherol acetate: 0.1%
Emalex RWIS-158 (isostearic acid PEG-58 hydrogenated castor oil): 2.0%
Eldew PS-306 (lauroyl glutamic acid di(octyldodecyl)phytosteryl/behenyl)): 0.5%
Butylparaben: 0.1%
Methylparaben: 0.2%
1,3-Butylene glycol: 5.0%
Purified water: balance According to this test example, toilet lotion that exhibited excellent adhesion to skin was obtained by incorporating the cationized hyaluronic acid obtained in Example 1.

6.26. Test Example 23

Preparation of Cosmetic Preparation

In this test example, whitening toilet lotion containing the cationized hyaluronic acid obtained in Example 1 was prepared according to the following formulation.
Cationized hyaluronic acid (Example 1): 0.1%
Acetylated hyaluronic acid: 0.1%
Arbutin: 2.0%
Elastin: 0.1%
Collagen peptide: 0.1%
Ethanol: 9.0%
Jojoba oil: 0.1%
Polyoxyethylene methyl glucoside: 1.0%
Polyglyceryl diisostearate: 0.2%
Citric acid: 0.1%
Sodium citrate: 0.2 g
Dipotassium glycyrrhizinate: 0.1%
Trisodium edetate: 0.1%
Propylparaben: 0.05%
Butylparaben: 0.05%
Methylparaben: 0.1%
Pentylene glycol: 3.0%
Arginine hydrochloride: 0.1%
Potassium 4-methoxysalicylate: 1.0%
2-Ethylhexyl p-methoxycinnamate: 0.01%
Essence: proper quantity
Purified water: balance According to this test example, whitening toilet lotion that exhibited excellent adhesion to skin was obtained by incorporating the cationized hyaluronic acid obtained in Example 1.

6.27. Test Example 24

Preparation of Cosmetic Preparation

In this test example, milky lotion containing the cationized hyaluronic acid obtained in Example 1 was prepared according to the following formulation.
Cationized hyaluronic acid (Example 1): 0.3%
Polyquaternium-51: 0.1%
Propylene glycol: 7.9%
Trehalose: 0.03%
Ceramide: 0.1%
Mineral oil: 3.0%
Trioctanoin: 1.5%
Squalene: 1.0%

Stearic acid: 0.5%
Cetearyl alcohol: 0.5%
Lanolin: 0.3%
Paraffin: 0.2%
Sorbitan stearate: 1.4%
Tetra oleate Solbase-30: 1.0%
Polysorbate 60: 0.8%
Methylparaben: 0.2%
Propylparaben: 0.1%
Ethanol: 0.01%
Phenoxyethanol: proper quantity
Carbomer: 0.1%
Potassium hydroxide: 0.1%
BHT: 0.02%
Tocopherol: proper quantity
Sodium EDTA-2: 0.02%
Purified water: balance According to this test example, milky lotion that exhibited excellent adhesion to skin was obtained by incorporating the cationized hyaluronic acid obtained in Example 1.

6.28. Test Example 25

Preparation of Cosmetic Preparation

In this test example, a pack (gel pack) containing the cationized hyaluronic acid obtained in Example 2 was prepared according to the following formulation.
Cationized hyaluronic acid (Example 1): 1.5%
Polyvinyl acetate emulsion: 17.0%
Polyvinyl alcohol: 11.0%
Sorbitol: 5.0%
Polyethylene glycol 400: 5.0%
Jojoba oil: 3.0%
Squalene: 2.5%
POE sorbitan monostearate: 1.0%
Titanium oxide: 4.0%
Talc: 8.0%
Ethanol: 8.0%
Bergamot: proper quantity
Paraben: proper quantity
Purified water: balance According to this test example, a pack (gel pack) that exhibited excellent adhesion to skin was obtained by incorporating the cationized hyaluronic acid obtained in Example 1.

6.29. Test Example 26

Preparation of Cosmetic Preparation

In this test example, vanishing cream containing the cationized hyaluronic acid obtained in Example 1 was prepared according to the following formulation.
Cationized hyaluronic acid (Example 1): 0.4%
Squalene: 11.0%
Dimethicone: 1.0%
Behenyl alcohol: 3.0%
Dioctyldodecyl lauroyl glutamate: 2.0%
Emalex GMS-50 (glyceryl stearate (SE)): 8.0%
Emalex 805 (PEG-5 stearate): 2.0%
Coenzyme Q10: 0.03%
Platinum nanocolloid: 0.01%
Propylparaben: 0.1%
Propylene glycol: 5.0%
Methylparaben: 0.2%
Urea: 5.0%
Purified water: balance According to this test example, vanishing cream that exhibited excellent adhesion to skin was obtained by incorporating the cationized hyaluronic acid obtained in Example 1.

6.30. Test Example 27

Preparation of Cosmetic Preparation

In this test example, cleansing cream containing the cationized hyaluronic acid obtained in Example 1 was prepared according to the following formulation.
Cationized hyaluronic acid (Example 1): 0.5%
Mineral oil: 30.0%
Paraffin: 3.0%
Beeswax: 2.0%
Cetyl octanoate: 25.0%
Behenyl alcohol: 5.0%
Glyceryl stearate: 1.0%
Emalex 600di-ISEX (PEG-12 diisostearate): 3.0%
Emalex 620 (Steareth-20): 1.0%
Tocopherol acetate: 0.1%
Propylparaben: 0.15%
Sodium stearoyl glutamate: 0.4%
1,3-Butylene glycol: 3.0%
Methylparaben: 0.15%
Xanthan gum: 10.0%
Purified water: balance According to this test example, cleansing cream that exhibited excellent adhesion to skin was obtained by incorporating the cationized hyaluronic acid obtained in Example 1.

6.31. Test Example 28

Preparation of Cosmetic Preparation

In this test example, a foundation containing the cationized hyaluronic acid obtained in Example 1 was prepared according to the following formulation.
Cationized hyaluronic acid (Example 1): 0.2%
Ethanol: 10.0%
Menthol: 0.02%
Glycerol: 5.0%
BG: 3.0%
Dimethicone: 2.0%
Trioctanoin: 2.0%
Dimethyl octyl PABA: 0.5%
Oxybenzone: 0.05%
Carbomer: 0.3%
Silica: 0.2%
AMP: 0.2%
Methylparaben: 0.16%
Phenoxyethanol: proper quantity
Tocopherol: 0.02%
Sodium EDTA-2: 0.01%
Purified water: balance According to this test example, a foundation that exhibited excellent adhesion to skin was obtained by incorporating the cationized hyaluronic acid obtained in Example 1.

6.32. Test Example 29

Preparation of Cosmetic Preparation

In this test example, lip cream containing the cationized hyaluronic acid obtained in Example 1 was prepared according to the following formulation.

Cationized hyaluronic acid (Example 1): 0.6%
Microcrystalline wax: 1.5%
Ceresin: 12.0%
Squalene: 10.0%
Decamethyltetrasiloxane: 10.0%
Diisostearyl malate: 5.0%
Candelilla wax: 2.0%
Vaseline: 8.0%
Glyceryl hydroxystearate: 2.0%
Tocopherol acetate: 0.3%
Menthol: 0.05%
Tocopherol: proper quantity
Liquid paraffin: proper quantity
Purified water: balance According to this test example, lip cream that exhibited excellent adhesion to skin was obtained by incorporating the cationized hyaluronic acid obtained in Example 1.

6.33. Test Example 30

Preparation of Cosmetic Preparation

In this test example, shaving lotion containing the cationized hyaluronic acid obtained in Example 1 was prepared according to the following formulation.
Cationized hyaluronic acid (Example 1): 0.5%
Dimethylsilanol hyaluronate: 0.1%
Ethanol: 58.0%
Menthol: 0.1%
Propylene glycol: 2.0%
Glycyrrhizinate dipotassium: 0.05%
Essence: 0.1%
Purified water: balance According to this test example, shaving lotion that exhibited excellent adhesion to skin was obtained by incorporating the cationized hyaluronic acid obtained in Example 1.

6.34. Test Example 31

Preparation of Cosmetic Preparation

In this test example, after-sun lotion containing the cationized hyaluronic acid obtained in Example 1 was prepared according to the following formulation.
Cationized hyaluronic acid (Example 1): 0.5%
Ethanol: 11.04%
BG: 4.16%
*Scutellaria* root extract: proper quantity
Stearyl alcohol: 0.72%
Avocado oil: 0.72%
Stearic acid: 0.02%
Orizanol: proper quantity
Polysorbate: 0.23%
PPG-6 decyltetradeses-20: 0.2%
4 Octoxynol 3: 0.08%
Methylparaben: 0.14%
Propylparaben: 0.07%
Carbomer: 0.13%
PVP: proper quantity
Potassium hydroxide: 0.04%
Sodium EDTA-2: 0.01%
Tocopherol: proper quantity
Purified water: balance According to this test example, after-sun lotion that exhibited excellent adhesion to skin was obtained by incorporating the cationized hyaluronic acid obtained in Example 1.

6.35. Test Example 32

Preparation of Cosmetic Preparation

In this test example, a bath additive containing the cationized hyaluronic acid obtained in Example 1 was prepared according to the following formulation.
Cationized hyaluronic acid (Example 1): 0.2%
Cetyl octanoate: 43.8%
Octyldodeceth-10: 8.0%
Butylparaben: 0.2%
Methylparaben: 0.1%
Glycerol: 2.0%
Purified water: balance According to this test example, a bath additive that exhibited excellent adhesion to skin was obtained by incorporating the cationized hyaluronic acid obtained in Example 1.

The invention claimed is:

1. A cationized hyaluronic acid and/or a salt thereof comprising a group shown by the following general formula (1) and having a degree of cationization of 0.15 to 0.6,

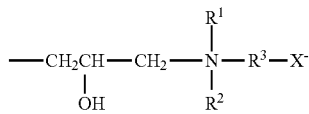

wherein $R^1$ to $R^3$ individually represent hydrocarbon groups, and $X^-$ represents a monovalent anion.

2. The cationized hyaluronic acid and/or a salt thereof according to claim 1, wherein the group is bonded to an oxygen atom of a (—C(=O)O—) group.

3. The cationized hyaluronic acid and/or a salt thereof according to claim 2, wherein the group is obtained by reacting a carboxyl group included in hyaluronic acid and/or a salt thereof with a cationizing agent that contains a quaternary ammonium group.

4. The cationized hyaluronic acid and/or a salt thereof according to claim 3, wherein the cationizing agent is at least one of a 2,3-epoxypropyltrialkylammonium halide and a 3-halogeno-2-hydroxypropyltrialkylammonium halide.

5. A hair modifying agent comprising the cationized hyaluronic acid and/or a salt thereof according to claim 1.

6. The hair modifying agent according to claim 5, wherein the cationized hyaluronic acid and/or a salt thereof has a degree of cationization of 0.15 to 0.4.

7. The hair modifying agent according to claim 5, wherein the hair modifying agent is used for a leave-in hair cosmetic preparation, and the cationized hyaluronic acid and/or a salt thereof has a degree of cationization of 0.15 to 0.4 and a kinematic viscosity (0.2% aqueous solution) of 5 to 50 mm$^2$/s.

8. The hair modifying agent according to claim 5, wherein the hair modifying agent is used for a rinse-out hair cosmetic preparation, and the cationized hyaluronic acid and/or a salt thereof has a degree of cationization of 0.4 to 0.6 and a kinematic viscosity (0.2% aqueous solution) of 1 to 20 mm$^2$/s.

9. The hair modifying agent according to claim 5, the hair modifying agent being used as a cuticle repairing agent.

10. A cosmetic preparation comprising the hair modifying agent according to claim 5.

11. A skin modifying agent comprising the cationized hyaluronic acid and/or a salt thereof according to claim 1.

12. A cosmetic preparation comprising the skin modifying agent according to claim 11.

13. A cosmetic preparation comprising the cationized hyaluronic acid and/or a salt thereof according to claim 1.

14. A method of producing a cationized hyaluronic acid and/or a salt thereof comprising reacting hyaluronic acid and/or a salt thereof with a cationizing agent in a water-containing medium, the water-containing medium being a base.

15. The method of producing a cationized hyaluronic acid and/or a salt thereof according to claim 14, further comprising adding at least one of a sodium salt and a potassium salt to the reaction solution and dissolving a solid produced in the reaction solution after reacting the hyaluronic acid and/or a salt thereof with the cationizing agent, and adding an alcohol to the reaction solution in which the solid is dissolved to obtain a precipitate.

16. The method of producing a cationized hyaluronic acid and/or a salt thereof according to claim 14, wherein the hyaluronic acid and/or a salt thereof is reacted with the cationizing agent by heating the water-containing medium at 30 to 70° C.

17. A cationized hyaluronic acid and/or a salt thereof shown by the following general formula (2),

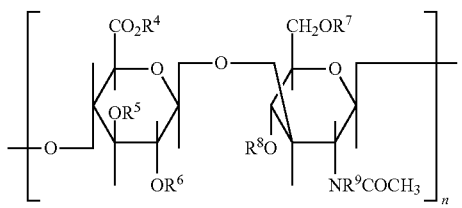

wherein $R^4$ to $R^9$ individually represent a hydrogen atom or a group shown by the following general formula (1), and n represents an integer from 2 to 5000,

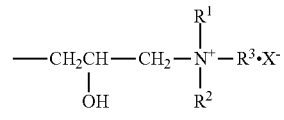

wherein $R^1$ to $R^3$ individually represent hydrocarbon groups, and $X^-$ represents a monovalent anion.

18. The cationized hyaluronic acid and/or a salt thereof according to claim 17, the cationized hyaluronic acid and/or a salt thereof having a degree of cationization of 0.15 to 0.6.

19. The hair modifying agent according to claim 7, the hair modifying agent being used as a cuticle repairing agent.

20. The hair modifying agent according to claim 8, the hair modifying agent being used as a cuticle repairing agent.

21. A cosmetic preparation comprising the hair modifying agent according to claim 7.

22. A cosmetic preparation comprising the hair modifying agent according to claim 8.

* * * * *